US010714219B2

(12) United States Patent
Altobello et al.

(10) Patent No.: US 10,714,219 B2
(45) Date of Patent: Jul. 14, 2020

(54) SYSTEM AND METHOD FOR UPLOADING AND SHARING MEDICAL IMAGES WITHIN TRUSTED HEALTH-USER COMMUNITIES

(71) Applicant: TIATROS INC., San Francisco, CA (US)

(72) Inventors: Daniel Altobello, San Francisco, CA (US); Kimberlie Cerrone, San Francisco, CA (US); Farid Agahi, San Francisco, CA (US)

(73) Assignee: Tiatros, Inc., San Francisco, CA (US)

( * ) Notice: Subject to any disclaimer, the term of this patent is extended or adjusted under 35 U.S.C. 154(b) by 539 days.

(21) Appl. No.: 14/744,489

(22) Filed: Jun. 19, 2015

(65) Prior Publication Data
US 2015/0286791 A1 Oct. 8, 2015

Related U.S. Application Data

(63) Continuation-in-part of application No. 13/096,887, filed on Apr. 28, 2011, and a continuation-in-part of
(Continued)

(51) Int. Cl.
G16H 80/00 (2018.01)
H04L 29/06 (2006.01)
(Continued)

(52) U.S. Cl.
CPC ........... *G16H 80/00* (2018.01); *G06F 19/321* (2013.01); *G06F 21/6263* (2013.01);
(Continued)

(58) Field of Classification Search
CPC ........ G06Q 50/22; G06Q 50/24; G06Q 10/10; G16H 80/00; G06F 19/00; G06F 21/6263;
(Continued)

(56) References Cited

U.S. PATENT DOCUMENTS 5,189,709 A 2/1993 Wang
5,664,109 A 9/1997 Johnson
(Continued)

FOREIGN PATENT DOCUMENTS

CA 2831300 A1 3/2012

OTHER PUBLICATIONS

International Search Report, European Search Report and Written Opinion, PCT/US2012/034498, dated Oct. 22, 2012.
(Continued)

Primary Examiner — Linh Giang Le

(57) ABSTRACT

Systems and methods of sharing medical images through a secure, HIPAA-compliant social network construct (CarePod) between two or more members of the CarePod are disclosed. A first user may communicate remotely with a CarePod that is created and associate with a patient having medical treatment in order to initiate the sharing of medical image(s) of a patient If the first user is not a member of the CarePod, the system may add the first user as a member of the CarePod through a verification/authentication process. Once authenticated, privileges of the first user may be set with respect to certain actions that the first user may perform with medical images. Medical image(s) may be shared asynchronously or streamed substantially in real-time—e.g., possibly to aid medical procedures that are occurring.

11 Claims, 11 Drawing Sheets

Related U.S. Application Data application No. 13/449,808, filed on Apr. 18, 2012, and a continuation-in-part of application No. 13/449,972, filed on Apr. 18, 2012, and a continuation-in-part of application No. 13/450,138, filed on Apr. 18, 2012.

(51) Int. Cl.

| | | |
|---|---|---|
| *G06F 19/00* | (2018.01) | |
| *H04W 4/21* | (2018.01) | |
| *G06Q 10/10* | (2012.01) | |
| *H04W 12/08* | (2009.01) | |
| *H04W 12/06* | (2009.01) | |
| *G06F 21/62* | (2013.01) | |
| *H04L 9/32* | (2006.01) | |
| *H04W 12/02* | (2009.01) | |
| *G06Q 50/22* | (2018.01) | |

(52) U.S. Cl.
CPC ........... *G06Q 10/10* (2013.01); *H04L 9/3213* (2013.01); *H04L 9/3234* (2013.01); *H04L 63/08* (2013.01); *H04L 63/0807* (2013.01); *H04L 63/102* (2013.01); *H04W 4/21* (2018.02); *H04W 12/02* (2013.01); *H04W 12/06* (2013.01); *H04W 12/08* (2013.01); *G06F 2221/2141* (2013.01); *G06Q 50/22* (2013.01); *H04L 2209/88* (2013.01)

(58) Field of Classification Search
CPC .......... G06F 19/321; G06F 2221/2141; H04W 4/21; H04W 12/06; H04W 12/08; H04L 9/3234; H04L 9/3213; H04L 63/0807; H04L 63/08; H04L 63/102; H04L 2209/88
See application file for complete search history.

(56) References Cited

U.S. PATENT DOCUMENTS

| | | |
|---|---|---|
| 7,051,120 B2 | 5/2006 | Greene |
| 9,411,936 B2 | 8/2016 | Landrum |
| 2002/0007321 A1 | 1/2002 | Burton |
| 2002/0010679 A1 | 1/2002 | Flesher |
| 2002/0032583 A1 | 3/2002 | Joao |
| 2002/0059379 A1 | 5/2002 | Harvey |
| 2002/0165758 A1 | 11/2002 | Hind |
| 2002/0165759 A1 | 11/2002 | Gruber |
| 2003/0009603 A1* | 1/2003 | Ruths ............... G06F 9/465 719/318 |
| 2003/0028399 A1 | 2/2003 | Davis |
| 2003/0036683 A1 | 2/2003 | Kehr |
| 2004/0015132 A1 | 1/2004 | Brown |
| 2004/0083428 A1* | 4/2004 | Slade ............ G06F 17/30873 715/205 |
| 2004/0111297 A1* | 6/2004 | Schoenberg .......... G06Q 10/10 705/3 |
| 2005/0149364 A1 | 7/2005 | Ombrellaro |
| 2005/0237577 A1 | 10/2005 | Alasia |
| 2006/0117378 A1 | 6/2006 | Tam |
| 2007/0106537 A1 | 5/2007 | Moore |
| 2007/0168228 A1 | 7/2007 | Lawless |
| 2007/0201101 A1 | 8/2007 | Corona |
| 2008/0040151 A1 | 2/2008 | Moore |
| 2008/0046286 A1 | 2/2008 | Halsted |
| 2008/0046984 A1* | 2/2008 | Bohmer ............ H04L 63/0853 726/5 |
| 2009/0319291 A1* | 12/2009 | Noordvyk .......... G06F 19/3425 705/2 |
| 2009/0326981 A1 | 12/2009 | Karkanias |
| 2009/0327857 A1 | 12/2009 | Hemmeryckx-Deleersnijder |
| 2010/0094652 A1 | 4/2010 | Dorsett |
| 2010/0256994 A1 | 10/2010 | Eisenberger |
| 2011/0046976 A1 | 2/2011 | Peruzzi |
| 2011/0087503 A1 | 4/2011 | Desai |
| 2011/0110568 A1* | 5/2011 | Vesper ................. G06F 19/321 382/128 |
| 2011/0119076 A1 | 5/2011 | Dhoble |
| 2011/0288874 A1 | 11/2011 | Hinkamp |
| 2015/0100335 A1 | 4/2015 | Englehard |

OTHER PUBLICATIONS

Canadian Examiner Report in CA2871713, dated Feb. 16, 2018.
Canadian Examiner Report in CA2871713, dated Feb. 3, 2020.
Indian Examiner Report in FER-1979-MUMN-2013, dated Sep. 25, 2019.

* cited by examiner

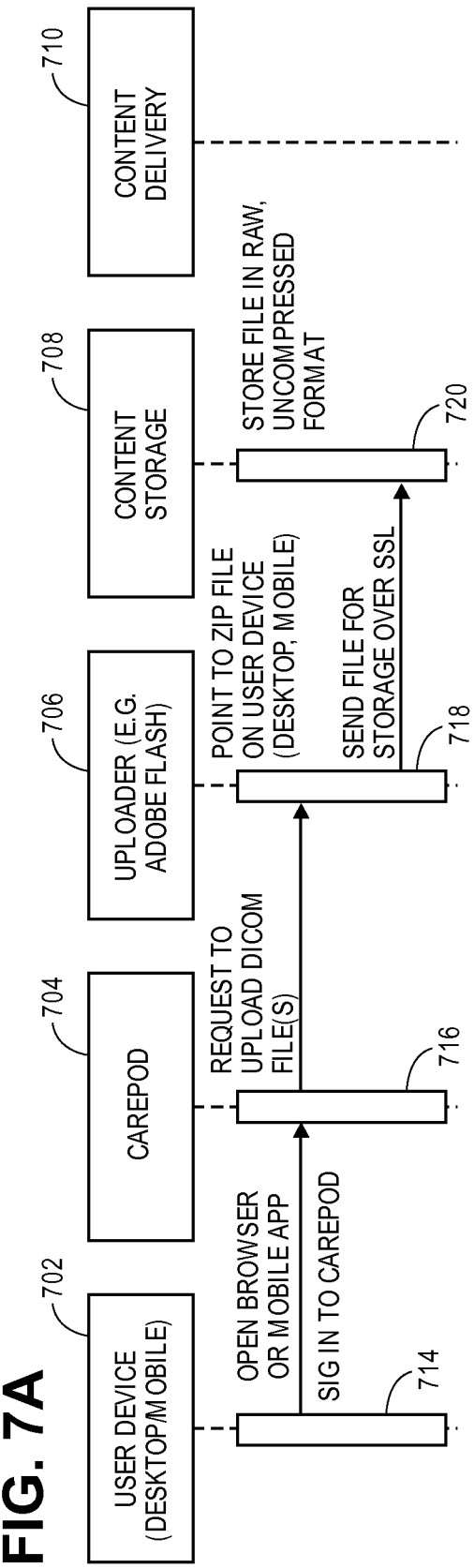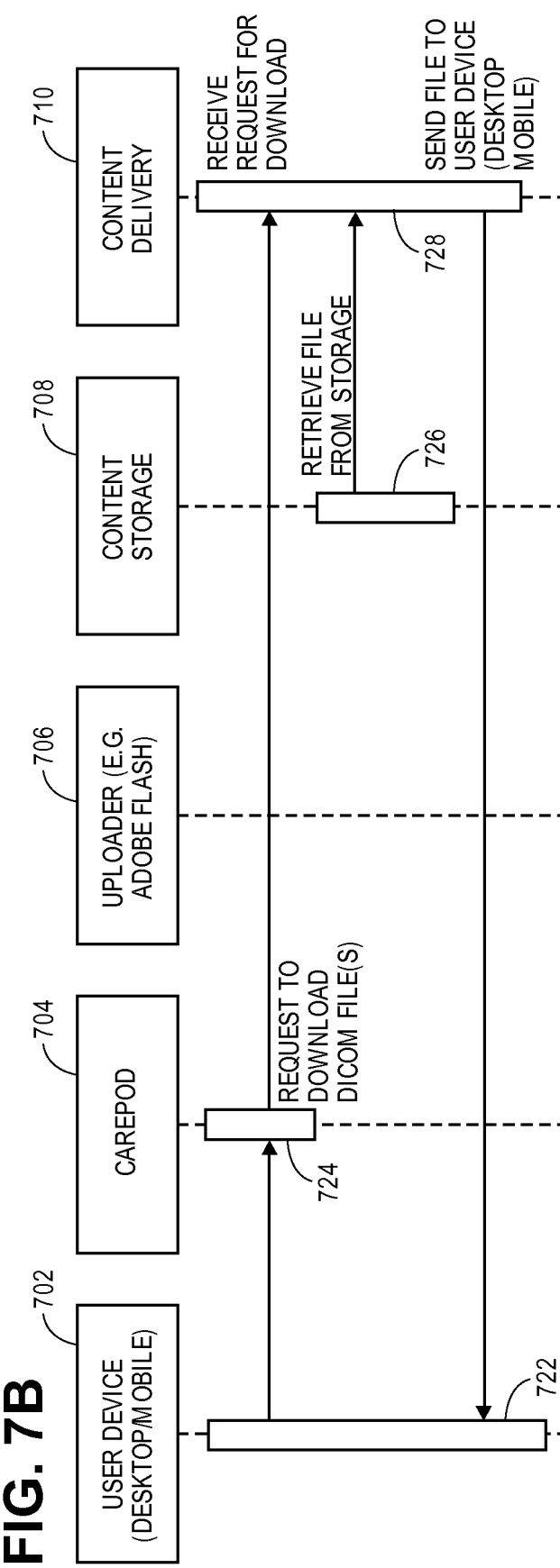

SYSTEM AND METHOD FOR UPLOADING AND SHARING MEDICAL IMAGES WITHIN TRUSTED HEALTH-USER COMMUNITIES

CROSS-REFERENCE TO RELATED APPLICATIONS

This Patent Application is a Continuation-in-Part (CIP) Application, and claims the benefit of, co-pending: (1) Application with a Ser. No. 13/096,887 filed by common Inventors of this Application on Apr. 28, 2011 and entitled "SYSTEM AND METHOD FOR CREATING TRUSTED USER COMMUNITIES AND MANAGING AUTHENTICATED SECURE COMMUNICATIONS WITHIN SAME" and published as United States Patent Application Publication Number 2012/0278101 (hereinafter the '101 Application); (2) Application with a Ser. No. 13/449,808 filed by common Inventors of this Application on Apr. 18, 2012 and entitled "SYSTEM AND METHOD FOR UPLOADING AND SECURING HEALTH CARE RECORDS TO TRUSTED HEALTH-USER COMMUNITIES" and published as United States Patent Application Publication Number 2012/0278103 (hereinafter the '103 Application); (3) Application with a Ser. No. 13/449,972 filed by common Inventors of this Application on Apr. 18, 2012 and entitled "SYSTEM AND METHOD FOR UPLOADING AND SECURING HEALTH CARE DATA FROM PATIENTS AND MEDICAL DEVICES TO TRUSTED HEALTH-USER COMMUNITIES" and published as United States Patent Application Publication Number 2012/0277543 (hereinafter the '543 Application); and (4) Application with a Ser. No. 13/450,138 filed by common Inventors of this Application on Apr. 18, 2012 and entitled "SYSTEM AND METHOD FOR CREATING AND MANAGING THERAPEUTIC TREATMENT PROTOCOLS WITHIN TRUSTED HEALTH-USER COMMUNITIES" and published as United States Patent Application Publication Number 2002/0278095 (hereinafter the '095 Application)—and all incorporated by reference in their entirety.

BACKGROUND

The sharing of medical image data has been an increasingly important in the effective treatment of a patient and his/her conditions. Patients are increasingly mobile—e.g., in terms of their physical presence (in moving from one place to another); but also in terms of their selection of physicians (in moving from one doctor to another). Another aspect is the need of primary physicians or other doctors to consult with specialists of one type or another. In yet another aspect, some entities (e.g., researchers, medical device companies) would like to have access to large number of medical images in order to improve treatments, size medical devices going into patients' bodies, or the like. In such cases, there is often a need to share medical imaging data—either for one patient, or a set of patients.

Although there are many forms and/or formats of digital image data and files, there has been a push in the medical industry to standardize this data. Today, Digital Imaging and Communications in Medicine (DICOM) is the standard for the communication and management of medical imaging information and related data.

With the introduction of computed tomography (CT) followed by other digital diagnostic imaging modalities in the 1970's, and the increasing use of computers in clinical applications, the American College of Radiology (ACR) and the National Electrical Manufacturers Association (NEMA) recognized the emerging need for a standard method for transferring images and associated information between devices manufactured by various vendors. These devices produce a variety of digital image formats.

The American College of Radiology (ACR) and the National Electrical Manufacturers Association (NEMA) formed a joint committee in 1983 to develop a standard to:

Promote communication of digital image information, regardless of device manufacturer Facilitate the development and expansion of picture archiving and communication systems (PACS) that can also interface with other systems of hospital information Allow the creation of diagnostic information data bases that can be interrogated by a wide variety of devices distributed geographically.

SUMMARY OF THE INVENTION

Several embodiments of the present invention comprise systems and methods of creating, managing and accessing treatment plans for patients having a condition are disclosed herein. Patients have CarePods created for the treatment of their condition and their doctors and other caregiver relevant to their treatment.

Systems and methods of sharing medical images through a secure, HIPAA-compliant social network construct (CarePod) between two or more members of the CarePod are disclosed. A first user may communicate remotely with a CarePod that is created and associate with a patient having medical treatment in order to initiate the sharing of medical image(s) of a patient If the first user is not a member of the CarePod, the system may add the first user as a member of the CarePod through a verification/authentication process. Once authenticated, privileges of the first user may be set with respect to certain actions that the first user may perform with medical images. Medical image(s) may be shared asynchronously or streamed substantially in real-time—e.g., possibly to aid medical procedures that are occurring.

In one embodiment, a method is disclosed comprising: receiving communications from a remote device, the remote device operated by a first user having a medical image to share with a second user within a CarePod created for a patient receiving medical treatment; if the first user is not a member of the CarePod, adding the first user to the CarePod; authenticating the first user as a member of the CarePod; granting a set of privileges to the first user for interacting with medical images within the CarePod; depending upon the set of privileges granted the first user, receiving medical image data from the first user; and sharing the medical image with the second user within the CarePod.

In another embodiment, a system for sharing medical image data of a patient receiving medical treatment is disclosed, wherein said patients and their caregivers are members of a trusted community of a CarePod, the system comprising: a CarePod module, said CarePod module configured to receiving communications from a remote device of a first user, the first user having a medical image to share with a second user of a CarePod, the CarePod created for a patient receiving medical treatment; and a user authentication module, said user authentication module configured to authenticating the first user as a member of the CarePod; and a user privileges module, said user privileges module configured to set privileges of the first user to perform actions regarding medical images of the patient.

Other features and advantages of the present system are presented below in the Detailed Description when read in connection with the drawings presented within this application.

BRIEF DESCRIPTION OF THE DRAWINGS

FIGS. 7A and 7B show one embodiment of flow charts for the management of the uploading and downloading of medical image files respectively.

DETAILED DESCRIPTION

Figure 1A:
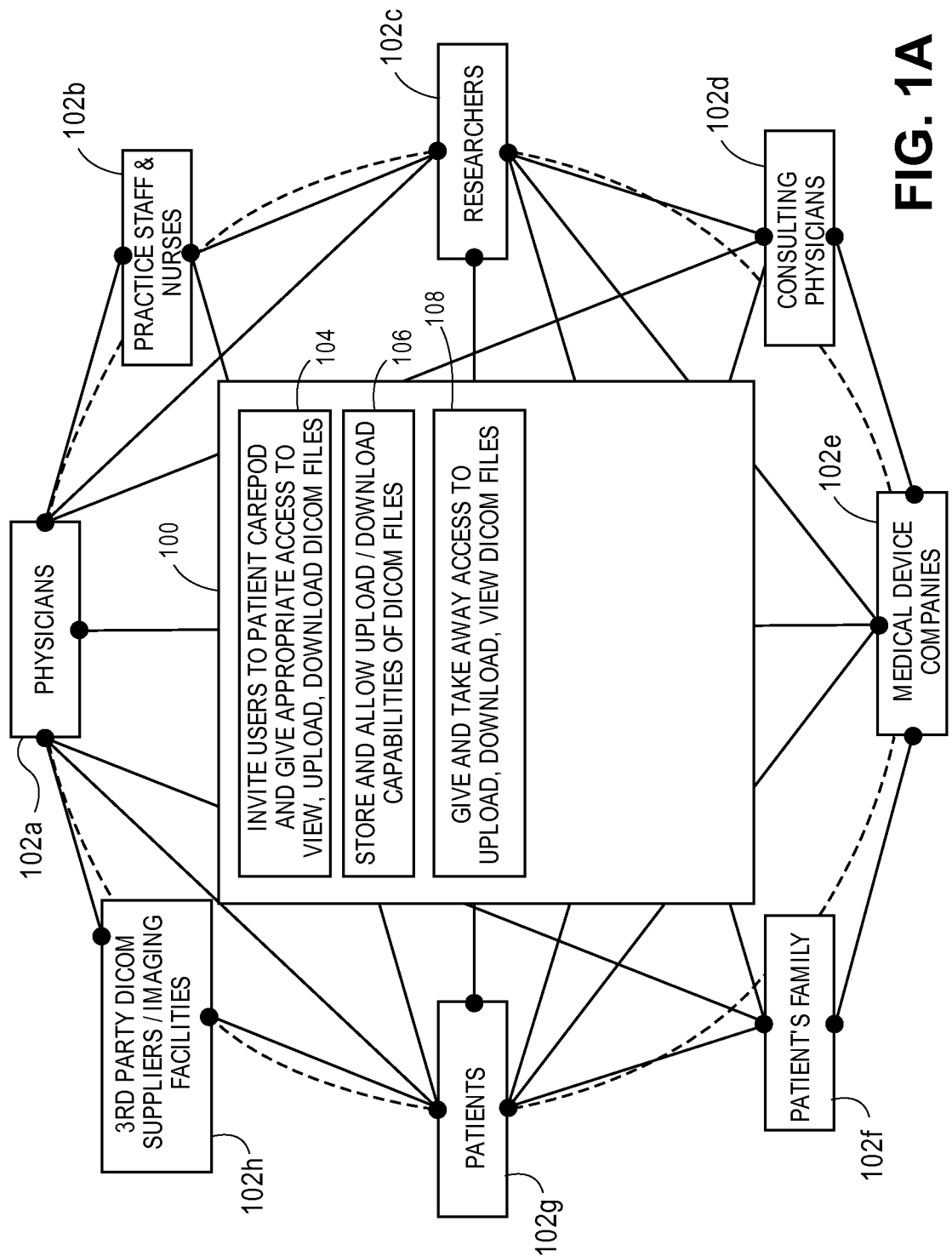
FIG. 1A shows a high level block diagram of a possible set of trusted users and possible modules for a system built in accordance with the principles of the present invention, and more particularly for medical applications built upon the system.

The need to share medical image files—such as, e.g., DICOM files—that contain Protected health information (PHI) requires a platform that may efficiently, effectively share this information between entities that desire them in a way that comports with Health Insurance Portability and Accountability Act (HIPAA).

Various Embodiments of CarePods

As hospitals and other HCPs promulgated internal regulations in response to the requirements of laws and regulations of HIPAA, one embodiment of the present invention helps HCPs comply with their internal regulations by providing for a networked system and method of managing the communications among a number of "trusted" users—e.g. by and between a physician and a patient.

In one embodiment, the present system comprises a versatile cloud computing software platform where doctors and researchers may use contemporary social networking tools to communicate with patients and the extended care team online, on tablets and via mobile phones, sharing personal health information and medical records within a HIPAA privacy and security compliant environment. The present system may be constructed as a rule-based computing system that insures that all trusted users and their interactions are compliant to federal, state and their own non-governmental (e.g. university, corporate or the like) privacy and security requirements. The present system should also be flexible to allow users (i.e. HCPs, issue groups or the like) to create specific on-line communities to address particular conditions, diseases or other health-related conditions or issues.

In another aspect of the flexibility, one embodiment of the present system should be to have the system available to users online, on tablets, and on mobile phones. This may be desirable in order to 'cross the digital divide' that separates low-income user/patients who do not have high-speed Internet access from health care and support services from which they may otherwise be excluded.

In one aspect, it is desirable to construct the present system in a versatile manner. For example, the present system may be used to construct and support many different types of specific-purpose online communities. The present system may incorporate one or many different types of social networking tools, including audio and video blogging and video chats, and other known types of synchronous and asynchronous communications. As literally hundreds of millions of Facebook, LinkedIn and Twitter users already know how to use social networking technology, the present system incorporates a suite of easy-to-use social networking functions, including audio and video blogging, text messaging and video chats, within a HIPAA-compliant online platform. This, in turn, greatly expanding the ability to connect clinical services to patients (and research studies to research subjects) in novel ways, remotely, cost-effectively, synchronously and asynchronously.

In addition, it is desirable that the present system incorporate content files into such communications—e.g. audio, video, medical application and any other commonly used documents or applications. The present system handles content files of any size, and content files that are created in virtually any underlying application, including the commonly used document, audio, video and specialized medical applications. It may be desirable for the present system to accurately preserve the fidelity of such files and records. The ability to use and share information and medical records within specific purpose communities creates the opportunity to develop new and efficient ways of using it.

In addition to the features listed above, it may also be desirable that the present system include other contemporary technologies to improve the user experience. For example, the use of avatars and other gaming technologies may increase the appeal of programs for some users, while other technologies may improve the user experience for veterans who are blind or hearing impaired.

Trusted Communities and/or Social Pods

In one possible aspect, the present embodiment may require that the physician communicate with a patient who is authenticated at the time of communication to the patient. In addition, the system stores and/or otherwise archives the interaction between the physician and the patient to form a part of the latter's EHR.

In another possible aspect, the present system may define a set of "trusted" users of the network. Such trusted users may need to be authenticated to establish their level of engagement and interaction with the system. Such authentication may be accomplished by any known method, manner or system for such authentication. Examples include password protection, challenge-response interactions, biometrics or the like.

As described further in the '101 Application, a Social/CarePod may comprise a set of entities that, in turn, might comprise a prototypical environment of trusted users. To share medical images, Social/CarePods Users (as depicted in FIG. 1A) (collectively labeled 102) are shown interconnectedly with the present system 100 and, possibly, connected amongst themselves apart from system 100. A set of users might comprise the following types of individuals: physicians 102a, practice staff and nurses 102b, researchers 102c, consulting physicians 102d, medical device companies 102e, patient's friends and family members 102f, patients 102g and third party medical image suppliers and/or imaging facilities 102h.

Each of the users 102 represent entities that may have known communication and computing devices (not shown) in order to affect a networked environment. For example, users 102 may variously have smart phones, cell phones, computers, tablets and the like that may be configured to run a secure, encrypted software environment, as might be presented in a browser or in any other known interfaces. It will be appreciated that the present system encompasses the use of all known devices and means of networked communication that would facilitate the present system as described herein.

The present system may also allow for easy dynamic management of the social pod. For example, the present system may allow for the addition and/or deletion of members in a seamless manner. To appreciate the flexibility of communities that the present system could enable, trusted communities might comprise one, two, or any number of members depending on their specific purpose. For mere exemplary purposes, communities may consist of:

a single member using a self-directed therapeutic intervention
   doctor+doctor
   doctor to pharmacy
   doctor to health insurance agent, e.g., for utilization review
   doctor+patient
   doctor+patient+family
   doctor+entire care team
   patient+entire care team
   doctor+multiple patients or multiple families
   research team
   research team+participants
   wellness program enrollees
   medical-educational program enrollees The identity of every participant in a community may be authenticated using one or more conventional identity authentication methods each time the member signs on to the community or accesses a content file. The present system may incorporate a variety of conventional authentication methods; the specific method(s) used to authenticate the members of a given community may vary as appropriate to its specific purpose.

Communities may be moderated, or self-directed. One or more moderators may oversee some types of programs, being able, for example, to add new members, remove objectionable content, and update content files. Other types of programs may be completely unsupervised and self-directed.

Because the present system may ensure HIPAA privacy and security compliance, communications and medical records that contain personal health information may be shared among members of the community, synchronously and asynchronously, online and on tablets and mobile phones.

In addition to setting up and populating trusted communities, the present system may use a number of technical strategies to pre-set and enforce access rights to ensure the privacy of communications, and appropriately limit access to certain files. Easy-to-use and redundant methods assure that the moderator(s) exercise complete and dynamic control over which communications and medical records, or parts thereof, are available to everyone, and which are available only to a certain subset of the community.

As discussed in the '101 Application, a Social/CarePod system 100 may comprise a set of networked computers and/or processors—in communications possibly with computers, processors or mobile devices that are in the possession or under the control of the users 102. There are many desirable and optional features that system 100 provides to users 102 and to the various HCP that are connected to the users.

For example, to facilitate the uploading/downloading/sharing of medical images, system 100 may provide the following:

(1) invite users to patient CarePods (or other CarePods, like treatment or research based CarePods) and give appropriate access to view, upload, download DICOM files (104);

(2) store and allow upload/download capabilities of DICOM files (106); and (3) give and take away access to upload/download and/or view DICOM files, according to a number of possible conditions (108).

It will be appreciated that while the term "DICOM" will be used throughout the present application, that the present application considers any medical image (of any form and/or standard) to be under the scope of the present applications. In this respect, "DICOM" and "medical image file" may be used interchangeably.

One embodiment of analysis and optimization of the present system provides that the interactions of involving users and the present system provides a feedback mechanism to sharpen and improve the effectiveness of the system for treating or servicing its users. For example, one embodiment of the present system might be a Clinical Care and Education program that allows providers several means to capture the data about the effectiveness of their programs. The "social" interactions inherent in the solution may be captured by the system, for example as unstructured data. The built Query-Response service allows the system to get explicit feedback in a secure fashion. In addition, the Therapeutics module might allow the system to capture responses from their patients and participants e.g. level of pain, mood, etc., along with compliance data such as "Did you take all three dosages of the medicine, on time" etc. This data set allows the system and its designers (which could be the clinicians and researchers of the program itself) to look for correlation among a particular protocol and its effectiveness and make changes to their programs, be it therapeutics or course material, style of presentation, etc.

Figure 1B:
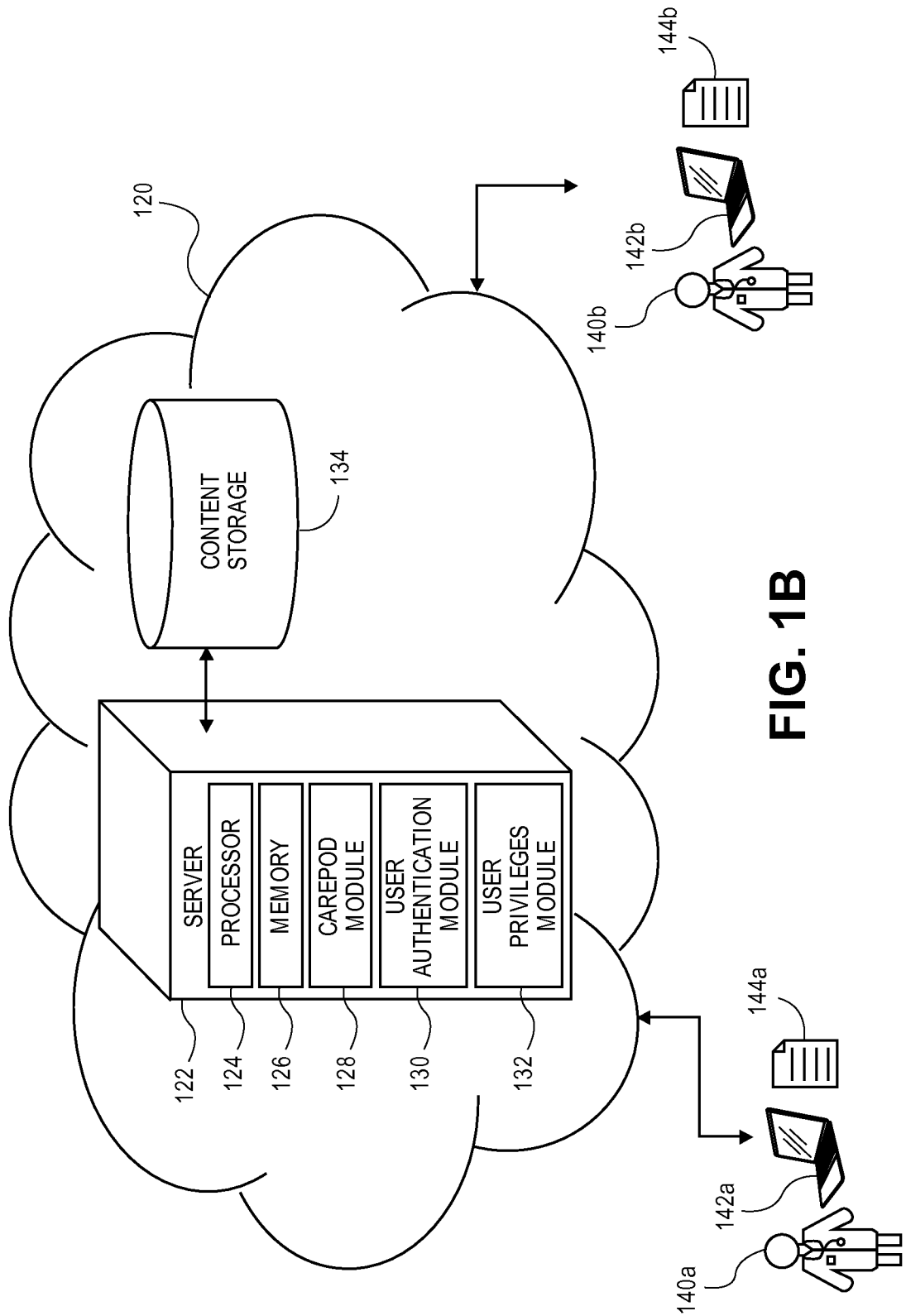
FIG. 1B shows one possible embodiment of a system architecture suitable for sharing medical image files remotely as made in accordance with the principles of the present application.

FIG. 1B shows one possible embodiment of system 100 to facilitate the effective sharing of medical image files. The system may comprise a server 122 in communication with a content storage/database 134. The server and storage may communicate with users (e.g., 140a, 140b) in any manner of wired or wireless configurations known in the art. One manner may be to have the server and content storage reside on the internet—e.g., possibly as a remote service 120 (e.g., cloud-based service, SaaS, or the like).

The server may further comprise a processor 124, a computer-readable storage 126 that may store computer-readable instructions for the processor to carry out any methods, algorithms, modules, etc.—to affect the present application. It will be appreciated that the present application may be hosted and/or executed on one or more processors (that may be remote from each other) and there may be many such computer readable memory storages that distribute the instructions and/or processing of the present application.

In some demonstrative embodiments, systems and/or machine-readable storage media may include one or more types of computer-readable storage media capable of storing data, including volatile memory, non-volatile memory, removable or non-removable memory, erasable or non-erasable memory, writeable or re-writeable memory, and the like. For example, machine-readable storage medium may include, RAM, DRAM, Double-Data-Rate DRAM (DDR-DRAM), SDRAM, static RAM (SRAM), ROM, programmable ROM (PROM), erasable programmable ROM (EPROM), electrically erasable programmable ROM (EEPROM), Compact Disk ROM (CD-ROM), Compact Disk Recordable (CD-R), Compact Disk Rewriteable (CD-RW), flash memory (e.g., NOR or NAND flash memory), content addressable memory (CAM), polymer memory, phase-change memory, ferroelectric memory, silicon-oxide-nitride-oxide-silicon (SONOS) memory, a disk, a floppy disk, a hard drive, an optical disk, a magnetic disk, a card, a magnetic card, an optical card, a tape, a cassette, and the like. The computer-readable storage media may include any suitable media involved with downloading or transferring a computer program from a remote computer to a requesting computer carried by data signals embodied in a carrier wave or other propagation medium through a communication link, e.g., a modem, radio or network connection.

In some demonstrative embodiments, logic may include instructions, data, and/or code, which, if executed by a machine, may cause the machine to perform a method, process and/or operations as described herein. The machine may include, for example, any suitable processing platform, computing platform, computing device, processing device, computing system, processing system, computer, processor, or the like, and may be implemented using any suitable combination of hardware, software, firmware, and the like.

In some demonstrative embodiments, logic may include, or may be implemented as, software, a software module, an application, a program, a subroutine, instructions, an instruction set, computing code, words, values, symbols, and the like. The instructions may include any suitable type of code, such as source code, compiled code, interpreted code, executable code, static code, dynamic code, and the like. The instructions may be implemented according to a predefined computer language, manner or syntax, for instructing a processor to perform a certain function. The instructions may be implemented using any suitable high-level, low-level, object-oriented, visual, compiled and/or interpreted programming language, such as C, C++, Java, BASIC, Matlab, Pascal, Visual BASIC, assembly language, machine code, and the like.

As part of the system, there may be a number of modules stored in the computer readable storage that affect the systems and methods of the present application. Among such possible modules, there may be a CarePod Module 128 to create and manage CarePods (as described herein), a User Authentication Module 130 to create and/or facilitate authentications and/or communications between users/entities/CarePods, and a User Privilege Module 132 to create and/or facilitate a set of privileges for the users of a CarePod/SocialPod—e.g., that would like to share medical images of a patient/CarePod member.

As may be seen, caregiver/user 140*a* may have a medical image 144*a* that (s)he might like to share with caregiver/user 140*b* (and deliver the image thereto as image 144*b*). In one embodiment, user 140*a* may access server 122, create a CarePod for a patient (or for user 140*b*) with CarePod module 128, authenticate a user (e.g., user 140*a*) with user authentication module 130 and/or set user privileges with user privilege module 132.

In merely one exemplary transaction involving FIG. 1A, user 104*a* may authenticate with server 122, upload medical image 144*a*, authorize user 104*b* to perform a number of functions with image 144*a* (depending on the privileges set for user 140*b*)—and possibly, enable user 140*b* to download, view, alter medical image 144*b* (depending upon the privileges set).

Further to this exemplary transaction, the server 122 may perform the following method:
 receiving communications from a remote device, the remote device (142*a*) operated by a first user (140*a*) having a medical image (144*a*) to share with a second user (140*b*) within a CarePod created for a patient receiving medical treatment;
 if the first user is not a member of the CarePod, adding the first user to the CarePod (e.g., by the administrator/physician/care provider of the CarePod);
 granting a set of privileges to the first user for interacting with medical images within the CarePod;
 authenticating the first user as a member of the CarePod;
 depending upon the set of privileges granted the first user, receiving medical image data from the first user; and
 sharing the medical image (144*b*) with the second user (140*b*) within the CarePod.

In this embodiment, it will be appreciated that the sharing of the medical image(s) may be performed on an asynchronous basis (e.g., where the sharing of the medical image(s) is not time sensitive)—or on a substantially real-time basis (e.g., where the medical images may be streamed to a second CarePod user). This may be desired in the case where a medical procedure (e.g. surgery and/or other medical intervention may be occurring and it is desired that a consultation be performed (e.g., by a radiologist or other specialists) while the procedure and/or intervention is being performed.

CarePod/SocialPod Creation and Management Infrastructure

Figure 2:
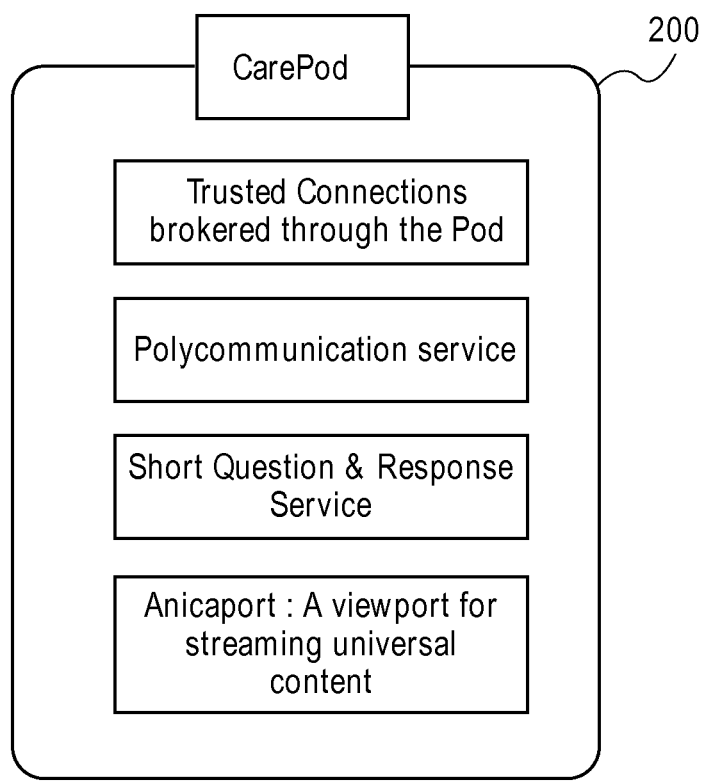
FIG. 2 depicts the concept of a social pod/CarePod as made in accordance with several of the present embodiments.

System 100 may be employed to create a networked "microcommunity" of users—a construct called a "social pod" and/or "CarePod". FIG. 2 depicts one exemplary social pod 200. Social pod 200 is enabled or otherwise hosted by system 100 as a set of interconnected computers, processors, mobile devices or the like. Desirable features of social pod 200 may include: a set of trusted connections brokered through the system; a polycommunication service (e.g. email, SMS, voicemail or the like); short question and response service; and a viewport and/or an application (called an "Anicaport" for purposes of this application, as described below). This Anicaport may act, at a high level, as a viewport for downloading, uploading, and/or streaming of content. Such content may be placed into appropriate formatting and made available to all or a subset of trusted users, possibly in some universal format. In one embodiment, a social pod may provide a restricted and secure way for a micro community of people organized around a specific outcome (e.g. clinical research, treatment of a medical condition, education for wellness etc.) to interact, collaborate, capture structured data, etc.

Figure 3:
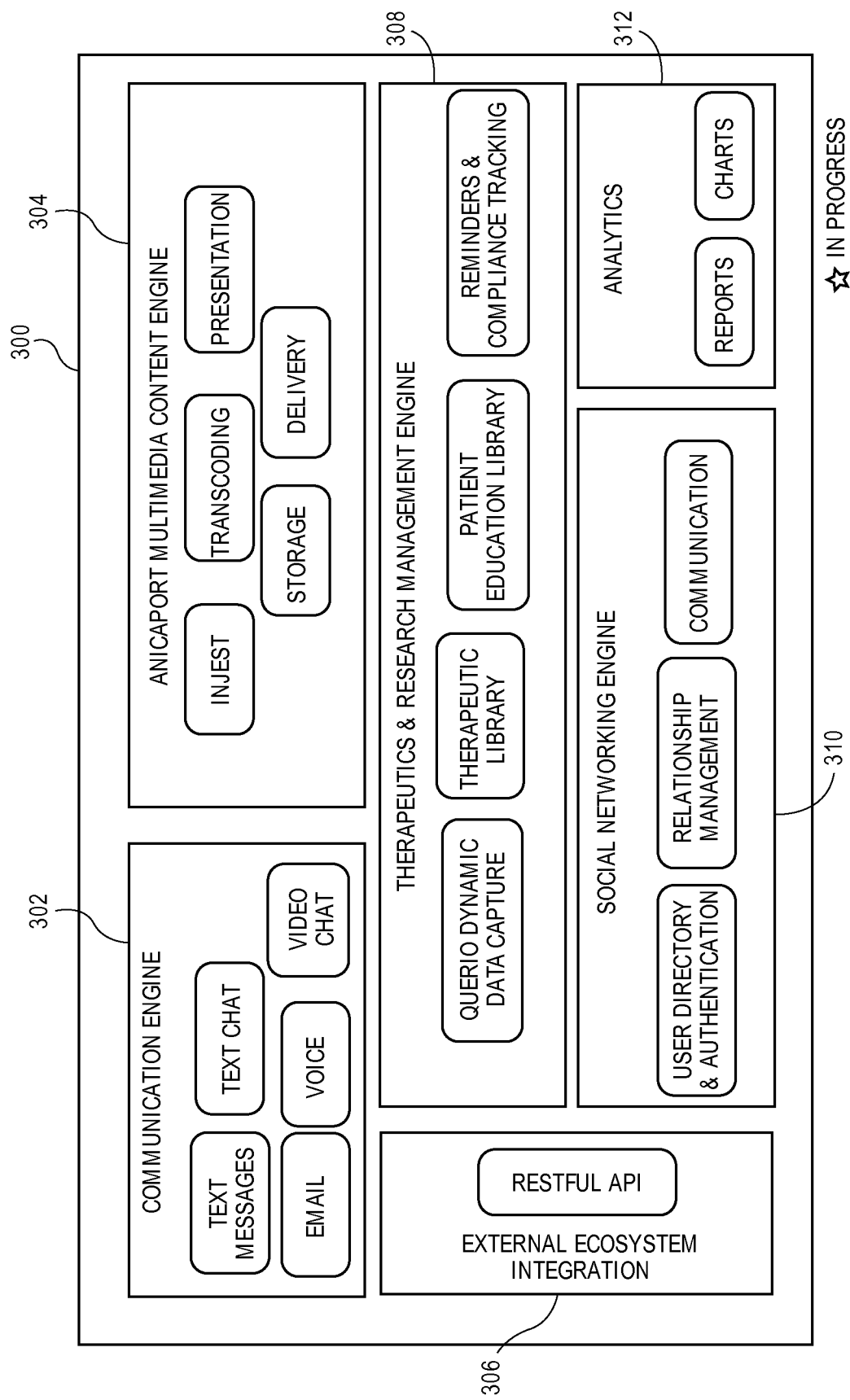
FIG. 3 is a high level block diagram of a system architecture for creating and managing CarePods according to the principles of the present application.

FIG. 3 depicts one embodiment of an architecture of a system that may perform in accordance with the teachings of the present invention. System 300 may advantageously comprise multiple modules for the creation and dynamic operation of the present system. Such modules may comprise the following: communication engine 302, multimedia content engine 304, external ecosystem integration module 306, therapeutic and research management engine 308, social networking engine 310 and analytic engine 312. Each module/engine will be discussed in turn below.

Communication engine 302 is the part of system 300 that comprises sufficient hardware and logic to setup and dynamically manage the flow of communications between trusted users of the present system. Communication engine 302 may manage communications from disparate means and modes of communications—e.g. text messages, chat, email, voice, video chat and the like.

Multimedia content engine 304 is that part of the system 300 that comprises sufficient hardware and logic to create, store, disseminate and dynamically manage the flow of data in and out of system 300 by and to trusted users of the system. Submodules of engine 304 might advantageously comprise: ingest submodule, transcoding submodule, presentation submodule, storage, and delivery submodules.

External ecosystem integration engine 306 may present a set of RESTful API, that allows it to exchange its data with third party systems and using (when applicable) industry standards such as HL7 etc. These API's will allow external systems to send information to the present system, e.g. a medical device or EHR system.

Therapeutics and Research Management Engine 308 is that part of the system 300 that comprises sufficient hardware and logic to create, store, disseminate, and dynamically manage treatment plans and pathways for trusted users on the system. It may be desirable for each trusted user of the system that is actively being treated via system 300 to be tracked by engine 308 and their progress logged and processed. Submodules of engine 308 may advantageously comprise: Querio dynamic data capture submodule, therapeutic library, patient education library, and reminders and compliance tracking submodule.

Social networking engine 310 is that part of system 300 that comprises sufficient hardware and logic to dynamically manage the various communications and relationships between trusted users of system 300. It should be appreciated that any known combination of processors, data structures, storage and communication media—including transport of data across networks, intranets, and the internet—may be utilized to affect the implementation of the present system, as is known to one skilled in the art.

One aspect of the present system is the ability to transcode, store, deliver and present content of a variety of media types. This would be desirable in any number of applications and context—and one such application is in the field of healthcare where patients may thrive better in a treatment program where use of multiple means of communications and messaging (both synchronous and/or asynchronous) may be applied. For example, a patient may not feel like talking directly to a doctor, or writing a lengthy email about conditions and results; but the patient might be amenable to uploading an audio or video file describing such. So, users and applications can use a multimedia content server/network—such as "Anicaport" to affect solutions.

It may also be desirable to create an Anicaport in such a way as to build solutions that may have shared content; but it is not desired to transmit the files multiple times. With Anicaport, content files of practically any size can be shared. The content files that are authored in native formats may be uploaded and shared, Anicaport may transcodes them to ensure that files will display in Web browser or Mobile device without the need for additional software. In addition, content files may be streamed and transmitted over secure, encrypted protocols and designed to be accessible from anywhere on the globe.

FIG. 3 depicts one embodiment of a method of creating a social pod. In this embodiment, the system may allow for a multi-part authentication procedure and mechanism. It will be appreciated, however, other mechanisms—with varying levels of authentication—may be set up and managed. It will be appreciated that the following description is merely by way of example and that other mechanisms and methods may be employed to create trusted communities and/or social pods.

Social pod 308 may be created by a provider, a physician or researcher 304 via the present system. Provider 304 alerts the system that a new "Care" pod is to be created and provider 304 may populate the pod by listing individuals (e.g. patient 306) and have the system invite patient 306 via some identified means of communication (e.g. by providing the patient's email address to the system) at 310. The system may manage social pod 308 as a set of data structures and/or routines to affect its creation and dynamic management. At 312, the system (via social pod 308 or the like) creates the new "Care" pod and adds patient 306 as a pod member, pending authentication. Pod 308 may then request the system to create patient as a User—in this example, via a request to the system's authentication module 302.

Authentication module 302 may perform such actions as shown at 314. To wit, module 302 may generate a security token and associate the token with the user's email address or any other identifier. Module 302 may return an invitation to the identified email address of the putative new user/patient 306. Patient/user 306 may then (at 316) access her email and confirm the address, setup a user password and enter other means of communication (e.g., a second communications pathway) for the system (such as mobile phone number, a second email address or the like). This other means of communication may be used to receive a second part authentication for the user. Once initial confirmation is received from patient/user 306, module 302 may confirm the token against the previously generated token (at 314) and send a text message to the mobile phone (or call the phone directly, or an email to the second, alternative, address or the like) with a second part token. Patient/user 306 may enter the second part token and return to module 302 for further authentication. If module 302 confirms the second part token, module 302 may signal to pod 308 that there is a trusted individual/user at 318.

Additional authentication means may optionally be set up, as desired. For example patient 306 may set up a voice recognition match for further authentication at 320, back to module 302. As time goes forward, patient 308 is then considered a trusted user and may access the pod with suitable credentials at 322.

In one embodiment, the present system may provide flexibility in setting up trusted relationships. For this, it may be desirable to establish that the forms of identifications provided by the user are indeed accessible by the user. For this, the present system may establish such multi-part authentication mechanism as desired. In addition, the administrators or providers of the system can choose the levels of authentication required for trusted users, with a basic minimum possibly designed.

System Architecture

Having described one aspect of the present system—i.e. the notion of trusted users and the social pod, one or more suitable architecture embodiments for the construction of the present system will now be described. In addition, it will be shown how one embodiment of the present system may leverage existing internet and other infrastructures for efficient build-out of the present system.

FIG. 4 depicts one embodiment of an architecture of a system that may perform in accordance with the teachings of the present invention. System 400 may advantageously comprise multiple modules for the creation and dynamic operation of the present system. Such modules may comprise the following: communication engine 402, multimedia content engine 404, external ecosystem integration module 406, therapeutic and research management engine 408, social networking engine 410 and analytic engine 412. Each module/engine will be discussed in turn below.

Communication engine 402 is the part of system 400 that comprises sufficient hardware and logic to setup and dynamically manage the flow of communications between trusted users of the present system. Communication engine 402 may manage communications from disparate means and modes of communications—e.g. text messages, chat, email, voice, video chat and the like.

Multimedia content engine 404 is that part of the system 400 that comprises sufficient hardware and logic to create, store, disseminate and dynamically manage the flow of data in and out of system 400 by and to trusted users of the system. Submodules of engine 404 might advantageously comprise: ingest submodule, transcoding submodule, presentation submodule, storage, and delivery submodules.

External ecosystem integration engine 406 may present a set of RESTful API, that allows it to exchange its data with third party systems and using (when applicable) industry standards such as HL7 etc. These API's will allow external systems to send information to the present system, e.g. a medical device or EHR system.

Therapeutics and Research Management Engine 408 is that part of the system 400 that comprises sufficient hardware and logic to create, store, disseminate, and dynamically manage treatment plans and pathways for trusted users on the system. It may be desirable for each trusted user of the system that is actively being treated via system 400 to be tracked by engine 408 and their progress logged and processed. Submodules of engine 408 may advantageously comprise: Querio dynamic data capture submodule, therapeutic library, patient education library, and reminders and compliance tracking submodule.

Social networking engine 410 is that part of system 400 that comprises sufficient hardware and logic to dynamically manage the various communications and relationships between trusted users of system 400. It should be appreciated that any known combination of processors, data structures, storage and communication media—including transport of data across networks, intranets, and the internet—may be utilized to affect the implementation of the present system, as is known to one skilled in the art.

One aspect of the present system is the ability to transcode, store, deliver and present content of a variety of media types. This would be desirable in any number of applications and context—and one such application is in the field of healthcare where patients may thrive better in a treatment program where use of multiple means of communications and messaging (both synchronous and/or asynchronous) may be applied. For example, a patient may not feel like talking directly to a doctor, or writing a lengthy email about conditions and results; but the patient might be amenable to uploading an audio or video file describing such. So, users and applications can use a multimedia content server/network—such as "Anicaport" to affect solutions.

It may also be desirable to create an Anicaport in such a way as to build solutions that may have shared content; but it is not desired to transmit the files multiple times. With Anicaport, content files of practically any size can be shared. The content files that are authored in native formats may be uploaded and shared, Anicaport may transcodes them to ensure that files will display in Web browser or Mobile device without the need for additional software. In addition, content files may be streamed and transmitted over secure, encrypted protocols and designed to be accessible from anywhere on the globe.

In one exemplary dynamic operation embodiment, some application (under user control or otherwise) may make an ingest request—e.g. a live recording or upload or the like. Ingest API may store any metadata (if any) in storage or database and send the file associated with the request to storage.

This file or data may be queued for further processing, if needed. If the file or data is a form of a document (e.g. office, pdf, etc.), then transcoding engine may process and generate one or more versions, perhaps in different formats, such as image format (e.g. SVG & PNG). Any metadata associated with the transcoding, if any, may be updated in a database or storage. If the file or the data is either an audio or video file, then transcoding engine may process it to a different format—e.g. H.264. Any metadata generated there may also be stored as noted.

Transcoding engine may then send the processed data/file to storage (perhaps over SSL). In addition, the data/file may be distributed to content delivery network. If there is any update that is needed to earlier saved metadata, it may be accomplished as desired.

Over time, the same or different application may make a request for a presentation of stored content (to which the user or owner of the application has rights to). Such request may be made to a presentation API, which then may select a presentation player and initiated streaming content from content delivery network. Presentation API may then oversee such streaming data to application. All of this may be accomplished with the Anicaport or other parts of the system checking and enforcing authorizations and permissions—matching users/applications to content.

One embodiment of code that implements an Anicaport—as well as the modules (e.g. 128, 130 and 132) that are employed in the sharing of medical images—are shown immediately below. It will be appreciated that many different implementations are possible and are contemplated within the scope of the present invention.

System Infrastructure

While the architecture of the present system presents one embodiment for the various modules that may be desirable in such a system, the present system itself may be hosted in a myriad of ways, to include leveraging existing infrastructures and the different companies that may provide services and hardware for such hosting and infrastructure.

Figure 5:
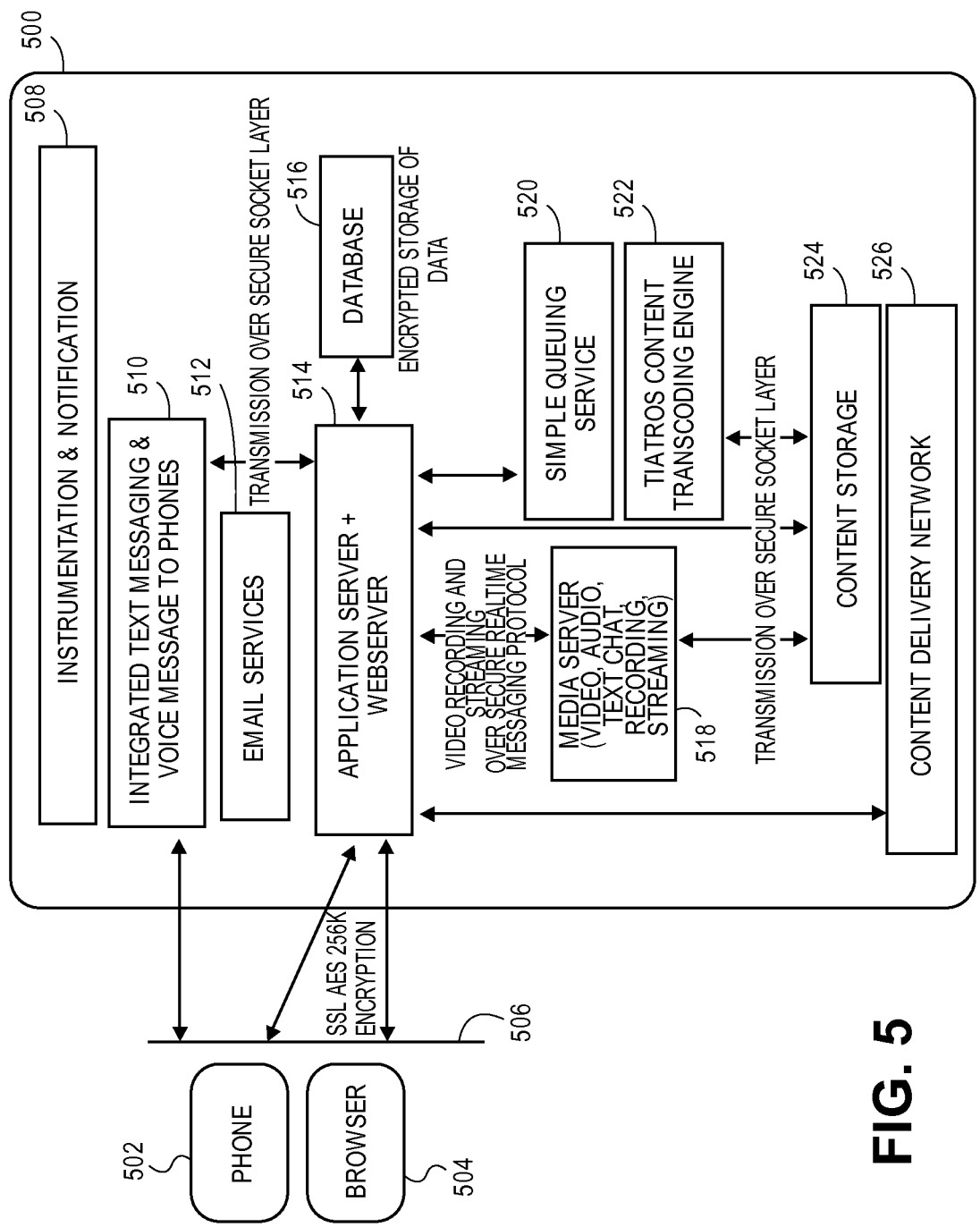
FIG. 5 depicts another embodiment of a system architecture of the present system as made in accordance with the principles of the present application.

FIG. 5 depicts one embodiment of the present system (500) as it may be hosted over existing infrastructure. Users of the present system may connect by a myriad of communication pathways. For example, users may connect via phone (502), mobile or otherwise, and by a browser 504 through standard interfaces 506. Once connected to the present system 500, the various modules of the present system may be a set of separately hosted modules that are in communication with one another.

The embodiment depicted in FIG. 5 has modules—instrumentation and notification module 508, integrated text and/or voice messaging 510, email service 512, application server and webserver 514, database 516, media server 518, simple queuing service 520, content transcoding engine 522, content storage 524 and content delivery network 526—interconnected in a manner in which each module may be separately hosted, or a set of such modules may be resident on a single site and/or processor.

In one embodiment, the present system may be built on top of best of breed infrastructure available from existing companies—e.g. database hosting services and cloud computing services. It may be desirable that the communication framework of the present system integrates with media servers, SMS gateways and voice capabilities.

In operation, content transcoding engine 522 may convert content files that are uploaded to content storage 524 in any format, e.g., Microsoft Office documents, pdf files, and various image and video formats, preparing them for direct preview and streaming delivery to computing devices, tablet or smartphones (without any downloads). The present system may also advantageously support the sharing of very large image and video content files such as ultrasounds and MRIs. In addition, the present system may also support parallel and separate communication threads among various subsets of a community, ensuring selective and appropriate access to communications, personal health information, and medical reports. The present system may automatically deposit every communication and medical record into a EHR and EMR repository. Notification engine 508 may support therapeutic reminders, workflows and communications.

For the sharing of medical images in one embodiment, system 500 may provide for image and/or video storage and/or streaming—e.g., over secure, real-time, messaging protocols. Such image data may flow between the application server 514 to/from media server 518.

Medical Image Processing Embodiments

Figure 4A:
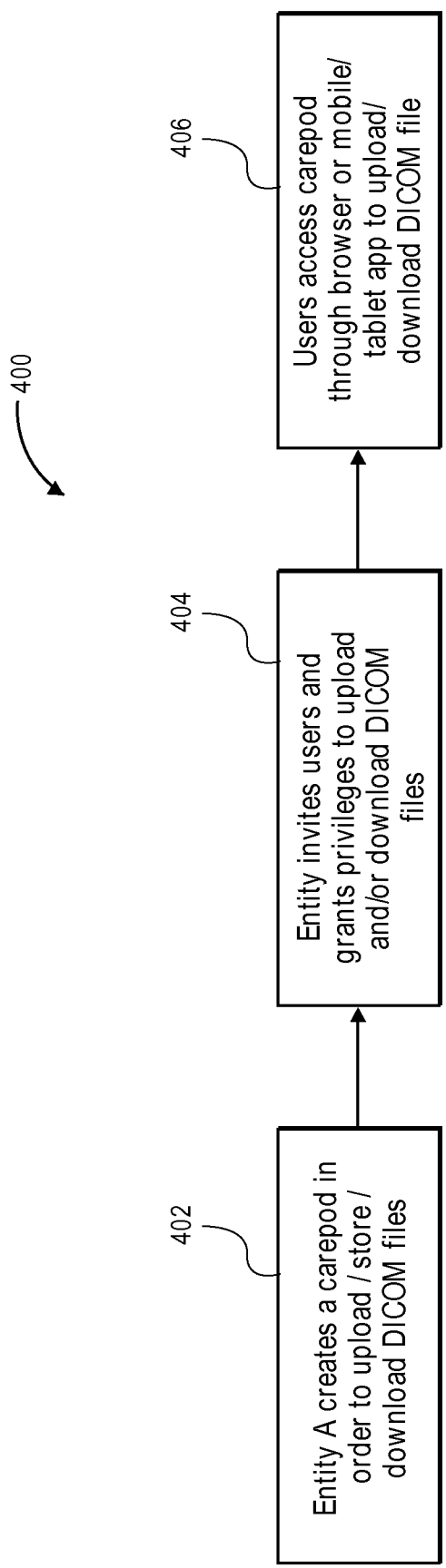
FIGS. 4A and 4B are flow charts of one embodiment for managing medical image sharing and de-identifying patient data, respectively.

FIG. 4A is one flowchart (400) of an exemplary process for sharing medical image data. At 402, a user (Entity A) may create a CarePod for the purpose of sharing medical image with other CarePod members/users. Entity A may use the above-described processes and mechanisms for the creation of such a CarePod. At 404, Entity A may invite users to the CarePod and grant privileges as to the medical image files. For example, other users/CarePod members may be allowed to upload, download, alter, annotate medical images, according to the privileges set by Entity A (or, possibly, some other CarePod member). At 408, authorized users/CarePod members may access the CarePod (and the medical images) through a browser (on a workstation, computer, laptop, mobile device or the like) to upload, download, alter, etc. the medical images as authorized.

Figure 4B:
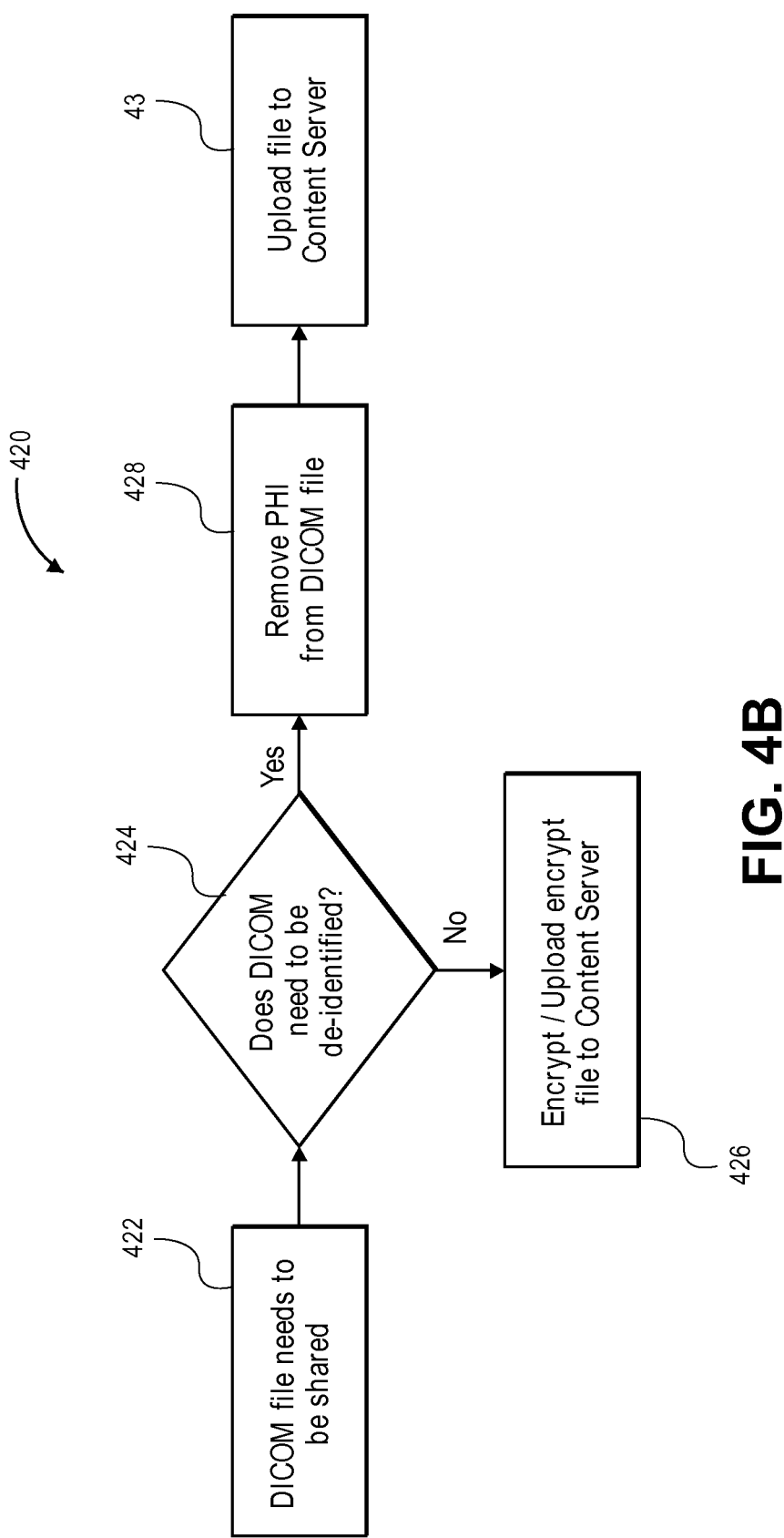

FIG. 4B depicts yet another medical image process flowchart (420) regarding removing patient identification information—possibly embedded in the medical image, or as associated metadata of the medical image. At 422, there may be a medical image that is desired to be shared; but it may be desirable to de-identify Personal Health Information (PHI) from the image and/or its metadata (queried at 424). If not, then the image may be uploaded to the content server at 426. The uploading may be encrypted to provide additional security, if desired.

If there is PHI to be removed from the image/metadata, then it is removed (at 428)—prior to uploading the image/metadata to the content server. As before, the file may be encrypted upon uploading for additional security, if desired.

Additional Processing Flowcharts

Figure 6:
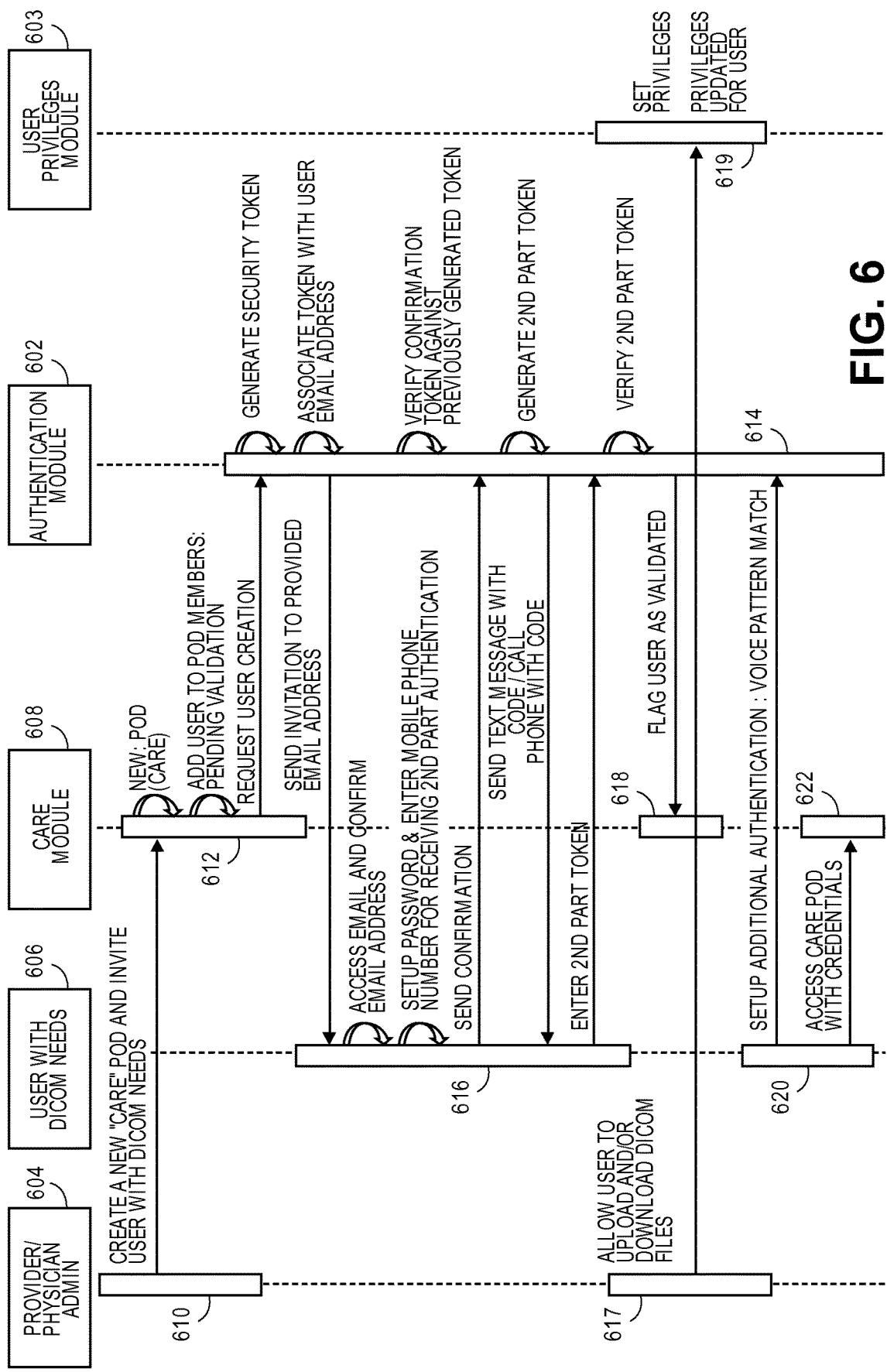
FIG. 6 shows one embodiment of a flow chart of the present system for authenticating and setting user privileges for the sharing of medical image files.

FIG. 6 depicts one flowchart embodiment that describes both a static and dynamic structure for the sharing of medical images.

Initially, at 604, a doctor/caregiver/etc. may desire to share a medical images with a user (606). As a potential first step, caregiver 604 may create a new CarePod at 610 and make an invitation to user 606. CarePod Module 608 may create the new CarePod at 612 and add users as CarePod members (possibly with a pending validation/authentication).

A request for user creation may be made to the authentication module 602. At this point, authentication module may take one or several of the following actions at 614. It could generate a security token, associate a token with user's email address and send it back to the user at 616. User may access and/or confirm the email address, set up password and/or enter mobile phone number (or some other communication path) for receiving $2^{nd}$ part authentication—and then send the confirmation back to the authentication module.

The authentication module may verify a confirmation token against the previously generated token. If verification is good, the module may generate the $2^{nd}$ part token to the user—who may enter the end part token in a return communication. If that is valid, then the authentication module may indicate to the CarePod module 608 that the user is valid.

The care member 604 may then allow the user to perform actions with medical image files at 617. Such actions may comprise: upload, download, annotate, modify, etc. The actions may be set as privileges at 619 with the user privileges module 603.

There may be other additional authentications that the user may be asked (or may perform) with the authentication module. For example, the user may set up a voice pattern match, a typing match, other biometrics or the like. The user may access the CarePod with any credentials that have been established.

Example of Use and Operation

Having described possible architectures and build-out of the present system, it will now be described the uses and operation of an exemplary system, built in accordance with the principles of the present invention.

FIGS. 7A and 7B depict two embodiments addressing the flow of operation of one such embodiment of the present system—i.e. the uploading and downloading of medical image files, respectively.

With reference to FIG. 7A, a user (on his/her device—e.g., mobile, smart phone, pad, laptop, desktop, etc.) may start communications with the CarePod 704 (e.g., opening a browser or other communications means) and sign into the CarePod at 714. CarePod 704 may receive a request to upload medical image files at 716 and refer the request to an uploader 706 (e.g., Adobe Flash or the like). Uploaded may point to a file (e.g. a zip file or other files) on the user's device and send the file for storage over any known protocol (e.g., SSL) at 718. Medical images may be stored in content storage 708—in any known format (e.g., raw, uncompressed format—or any other suitable format).

In FIG. 7B, a user may request to download medical image files of the CarePod 704. CarePod may forward that request to content delivery module 710. Content delivery 710 may request and/or retrieve file from content storage 708. The file may be send to the user's device at 728, completing the request.

Two Embodiments

Figure 8:
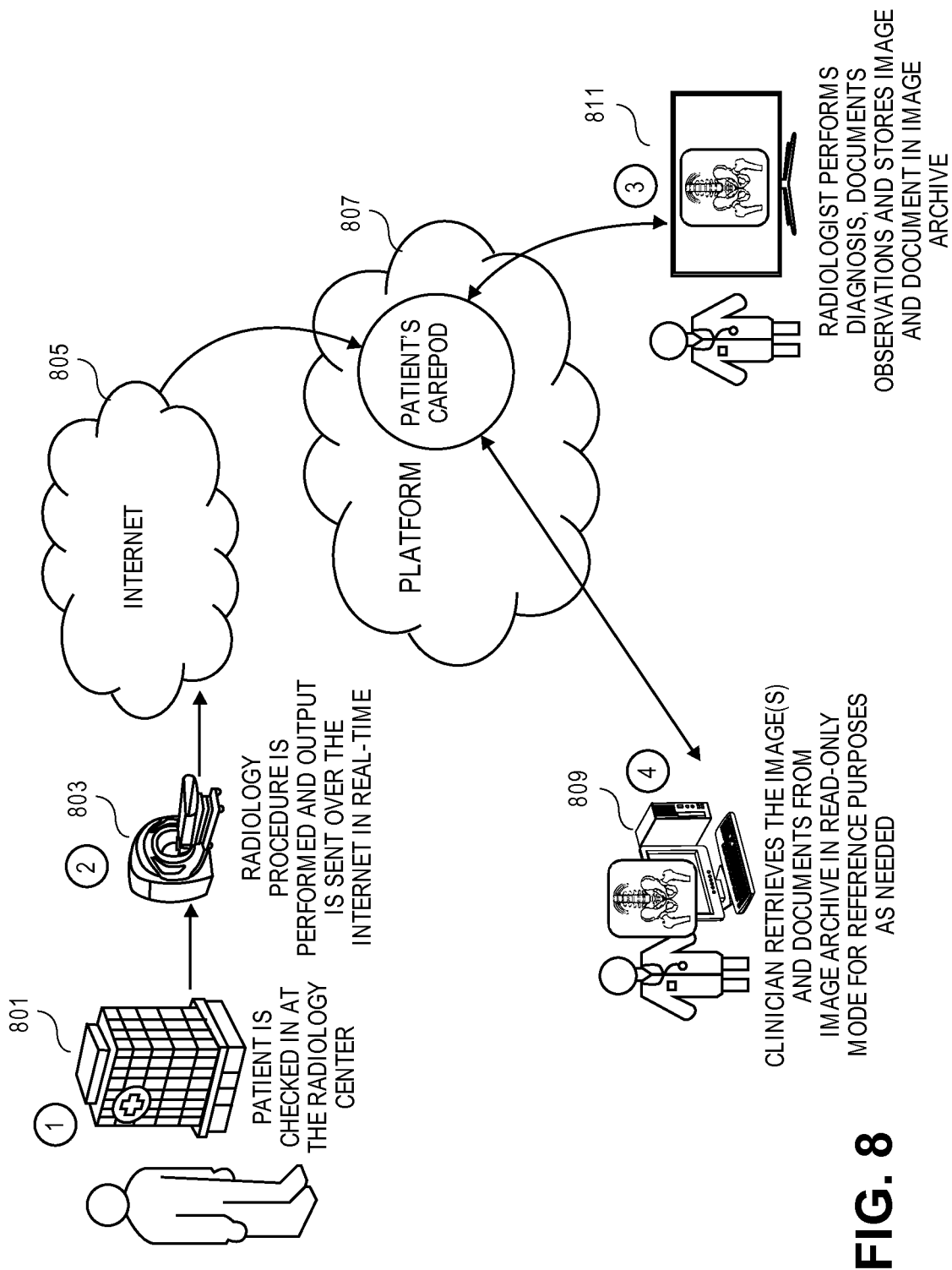
FIGS. 8 and 9 show one embodiment of the present system streaming medical images substantially in real time to affect a consultation between care providers on a substantially real time basis.

FIG. 8 is one possible embodiment of a use case for the present system. In this embodiment, a patient may be scheduled for a medical imaging appointment at a facility 801. At 803, the patient may be imaged (e.g., using any possible imaging modality known, including but not limited to: ultrasound, X-ray, CT, MRI or the like). The images may be captured and/or streamed in real-time, or near real-time over a network 805 (for example, the internet—or some other network). These images may be sent/streamed to the patient's CarePod (e.g., as may be hosted on the system platform 807, as described in any of the embodiments described herein).

At this point, the image data may be sent/streamed to a plurality of users. For example, the image may be sent to clinician 809 who may be attending to the patient either during imaging or when patient is being treated. Having such images may improve and/or alter the treatment that the patient may be receiving in substantially real-time. For another example, a radiologist 811 may be receiving the images in substantially real-time—e.g., in order to make diagnosis in a timely manner that may improve and/or alter the treatment that the patient may be receiving in substantially real-time.

Figure 9:
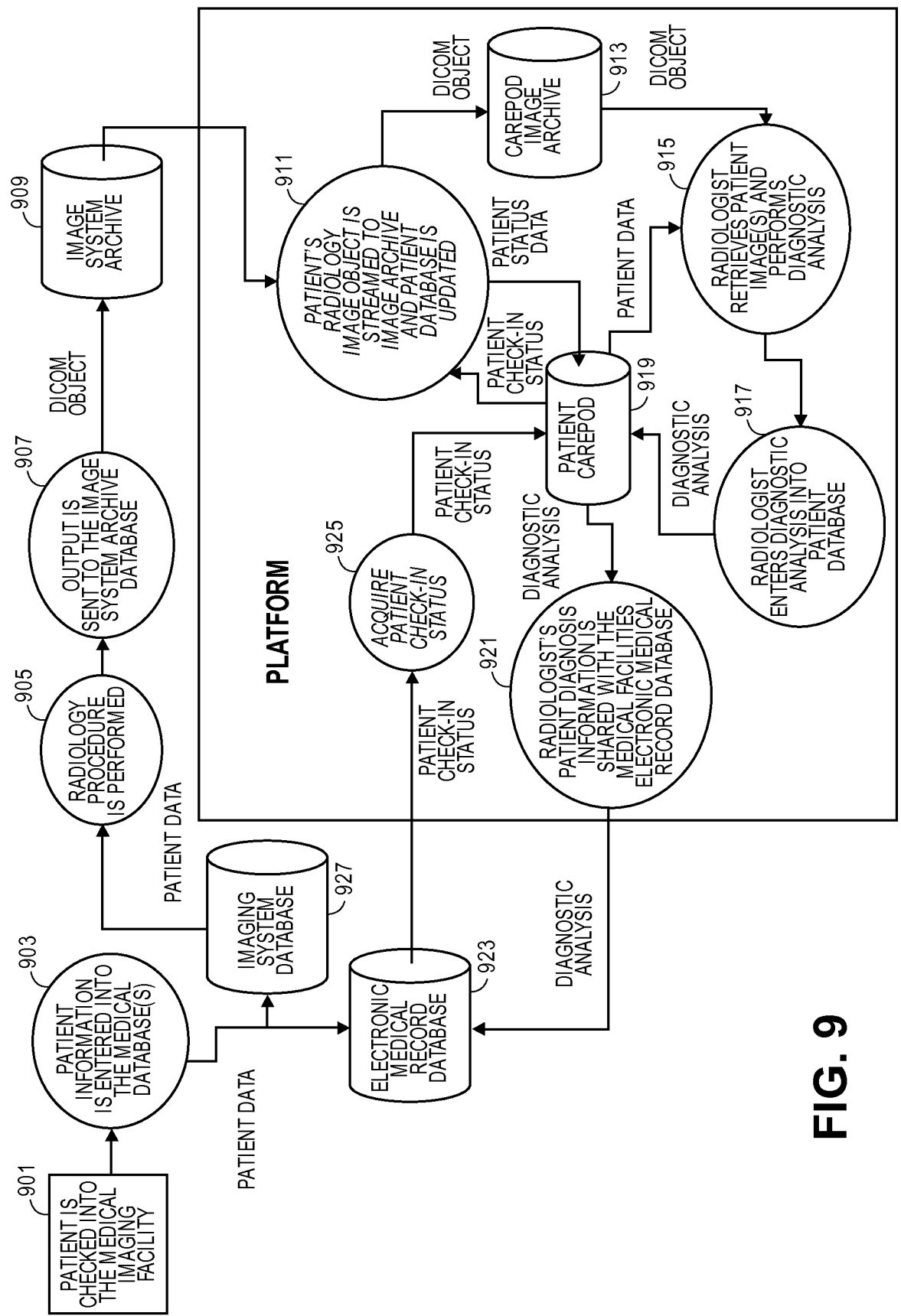

FIG. 9 depicts another possible embodiment of a flowchart where the patient may be undergoing medical imaging and how those images may be shared in substantially real-time. At 901, the patient may be checked into an imaging facility and his/her information may be entered at 903 into databases (e.g., imaging system database 927 and/or EMR database 923). This information may also be entered into his/her CarePod for dissemination to the CarePod members and team—e.g., at set 925 and at 919.

At 905, the patient may be imaged and the image data may be sent/streamed at 907. The image may be archived at 909—and/or streamed (911) to the CarePod 919 and CarePod image archive 913.

At 915, the medical image may be received by a radiologist for substantially real-time diagnosis (if desired) and may enter the diagnosis into a database at 917—which may be accessible to other CarePod members at 921 through CarePod 919.

At this point, if the patient is also being treated at nearly the same time as the imaging, other healthcare professionals may be able to change and/or improve the treatment for the patient.

A detailed description of one or more embodiments of the invention, read along with accompanying figures, that illustrate the principles of the invention has now been given. It is to be appreciated that the invention is described in connection with such embodiments, but the invention is not limited to any embodiment. The scope of the invention is limited only by the claims and the invention encompasses numerous alternatives, modifications and equivalents. Numerous specific details have been set forth in this description in order to provide a thorough understanding of the invention. These details are provided for the purpose of example and the invention may be practiced according to the claims without some or all of these specific details. For the purpose of clarity, technical material that is known in the technical fields related to the invention has not been described in detail so that the invention is not unnecessarily obscured.

TABLE 1 – ANICAPORT

Provider create
URL:
https://github.com/tiatros/tiatros/blob/stage/app/controllers/registrations_controller.rb
Line: 24

```
def create
  @user = User.new(params[:user])
  @provider = Provider.new(params[:provider])
  @provider.subdomain = params[:provider][:subdomain].downcase
  if verify_recaptcha
    @role = Role.find_by_name('administrator')
    @provider.contact_email= @user.email
    @Providermember = Providermember.new respond_to do |format|
      Provider.transaction do
        @provider.save
        if (@provider.errors.blank?)
          User.transaction do
            @user.save
            Providermember.create(:provider_id=>@provider.id,:user_id=>@user.id)
```

```
                Userrole.create(:user_id=>@user.id, :role_id=>@role.id ,:provider_id=>@provider.i
d)
            end
          end
          if (!@user.errors.blank?)
            raise ActiveRecord::Rollback
          end
        end if @user.errors.blank? && @provider.errors.blank?
          flash[:alert] = "Please confirm your account and login to personalize"
          format.html {redirect_to :controller=>'landing', :action => 'nextsteps'}
        else
          format.html {render :action => "new"}
        end
      end
    else
      build_resource
      clean_up_passwords(resource)

@user.errors.add "Security Error: ", "There was an error with the recaptcha code below.
Please re-enter the code and click submit."
      #flash[:recaptcha_error] = ""
      #flash[:alert] = "There was an error with the recaptcha code below. Please re-enter the
code and click submit."
      #render_with_scope :new
      render :action => :new
    end
  end
end
```

Anicaport
src / Anicaport_processor.rb
For file processing
URL: https://github.com/tiatros/Anicaport/blob/master/src/Anicaport_processor.rb

```
soffice --headless --accept="socket,host=127.0.0.1,port=8100;urp;" --nofirststartwizard & require File.expand_path(File.dirname(__FILE__) + '/config')
require File.expand_path(File.dirname(__FILE__) + '/../lib/convert_office')

class AnicaportProcessor
```

```
def initialize
  queue_name = UPLOAD_QUEUE

@sns = AWS::SNS.new
  @sqs = AWS::SQS.new
  @s3 = AWS::S3.new
  @sdb = AWS::SimpleDB.new
  @transcoder = AWS::ElasticTranscoder::Client.new @current_log = ""

domain = @sdb.domains.create(queue_name)
  uuids_processing = domain.items['files'].attributes['uuids_processing']
  uuids_failed = domain.items['files'].attributes['uuids_failed']

queue = @sqs.queues.create(queue_name)
  queue.poll(:batch_size => 1) do |msg| time_started = Time.now
    result = nil begin
      if !uuids_processing.values.include?(msg.body) && !uuids_failed.include?(msg.body)

added_to_db = false
        begin
          uuids_processing.add msg.body
          added_to_db = true
        rescue Exception => e
          # try next one by clear simpledb
          # uuids_processing.delete
          uuids_failed.delete
        end
        uuids_processing.add msg.body unless added_to_db result = self.process_msg(msg.body)
      end
    rescue Exception => ex
      print_to_error_log ex.message
      print_to_error_log ex.backtrace.join("\n")
      print_to_error_log "Error: Unknown error occurred processing: #{msg}"
```

```
    end begin
      uuids_processing.delete msg.body
      uuids_failed.add msg.body if !result self.report_status(queue_name, msg.body, time_started, Time.now, result)
    rescue Exception => ex
    end end
end def process_msg(msg)
  print_to_access_log "Notice: Got message to process: #{msg}"

begin
    url_regexp = /https?:\/\/\w/
    url = msg.split.grep(url_regexp)[0].strip
  rescue
  end unless url.blank?
    print_to_access_log "Notice: Detected URL: #{url}"
    msg = msg.gsub(url, " ").strip
  end bucket_name, full_object_path = msg.split('::')

print_to_access_log "bucket: #{bucket_name}"
  print_to_access_log "full_object_path: #{full_object_path}"
  print_to_access_log "url: #{url}" unless url.blank?

unless bucket_name.blank? || full_object_path.blank?
    @bucket = @s3.buckets.create("#{bucket_name}")
    if @bucket.objects["#{full_object_path}"].exists?
      process_file(bucket_name, full_object_path)
      return true
    elsif !url.blank?
      process_url(bucket_name, full_object_path, url)
```

```
    return true
  else
    print_to_error_log "Error: File does not exist in s3: #{msg}"
    return false
  end
 end
end def process_url(bucket_name, full_object_path, url)
 print_to_access_log "Notice: Processing URL: #{url}"

redirected_url = url begin
   redirected_url = open(redirected_url).base_uri.to_s
 rescue
   redirected_url = nil
 end url = redirected_url object_path_arr = full_object_path.split("/")
 if object_path_arr[0]=="common"
   object_uuid = object_path_arr[1]
   file_name = object_path_arr[3]
   provider_folder = object_path_arr[0]
 else
   object_uuid = object_path_arr[2]
   file_name = object_path_arr[4]
   provider_folder = object_path_arr[1]
 end file_basename = file_name.split('.').first
 file_extension = file_name.split('.').last account_dir = File.expand_path(File.dirname(__FILE__) + '/../kitchen/' + provider_folder)+"/"
   processing_dir = "#{account_dir}#{object_uuid}/"
   original_file_path = "#{processing_dir}original/#{file_name}"
```

```
    command "mkdir #{account_dir}" if File.exists?(account_dir) == false
    command "mkdir #{processing_dir}" if File.exists?(processing_dir) == false
    command "mkdir #{processing_dir}original/" if File.exists?("#{processing_dir}original/") ==
false
    command "mkdir #{processing_dir}processed/" if
File.exists?("#{processing_dir}processed/") == false
    command "mkdir #{processing_dir}thumbnail/" if
File.exists?("#{processing_dir}thumbnail/") == false
    command "mkdir #{processing_dir}tmp/" if File.exists?("#{processing_dir}tmp/") == false unless redirected_url.blank?
      capture_snapshot(url, original_file_path)
    else
      command "cp #{File.expand_path(File.dirname(__FILE__) + '/../images/')+"/404.jpg"}
#{original_file_path}"
    end snapshop_created = false
    if File.exists?(original_file_path)
        command "convert #{original_file_path} -thumbnail '500x500^' -background white -flatten
-alpha off -gravity center -extent 500x500
#{processing_dir}tmp/#{file_basename}.#{file_extension}"
        command "cp #{processing_dir}tmp/#{file_basename}.#{file_extension}
#{original_file_path}"

toamazon("#{full_object_path}", "#{original_file_path}")
      snapshop_created = true
    end command "rm -rf #{processing_dir}"

process_file(bucket_name, full_object_path) if snapshop_created
  end def process_file(bucket_name, full_object_path)
    print_to_access_log "Notice: Processing FILE: #{full_object_path}"

object_path_arr = full_object_path.split("/")
    if object_path_arr[0]=="common"
      object_uuid = object_path_arr[1]
      file_name = object_path_arr[3]
```

```
  provider_folder = "#{object_path_arr[0]}"
else
 object_uuid = object_path_arr[2]
 file_name = object_path_arr[4]
 provider_folder = "#{object_path_arr[0]}/#{object_path_arr[1]}"
end object_path = "#{provider_folder}/#{object_uuid}"

file_basename = file_name.split('.').first
file_extension = file_name.split('.').last account_dir = File.expand_path(File.dirname(__FILE__) + '/../kitchen/' + provider_folder)+"/"
 processing_dir = "#{account_dir}#{object_uuid}/"
 original_file_path = "#{processing_dir}original/#{file_name}"

command "mkdir #{account_dir}" if File.exists?(account_dir) == false
 command "mkdir #{processing_dir}" if File.exists?(processing_dir) == false
 command "mkdir #{processing_dir}original/" if File.exists?("#{processing_dir}original/") == false
 command "mkdir #{processing_dir}processed/" if File.exists?("#{processing_dir}processed/") == false
 command "mkdir #{processing_dir}thumbnail/" if File.exists?("#{processing_dir}thumbnail/") == false
 command "mkdir #{processing_dir}tmp/" if File.exists?("#{processing_dir}tmp/") == false chunk_size = 5_242_880 obj = @bucket.objects["#{full_object_path}"]
size = obj.content_length
byte_offset = 0

File.open(original_file_path, 'w') do |file|
  while byte_offset < size
    range = "bytes=#{byte_offset}-#{byte_offset + chunk_size - 1}"
    file.write(obj.read(:range => range))
    byte_offset += chunk_size
  end
end
```

```
if scanfile(original_file_path)
  begin delete_previous_processing(object_path)

if is_video?(file_extension)

pipeline_id = nil
      @transcoder.list_pipelines.pipelines.each do |p|
        if p.name == bucket_name
          pipeline_id = p.id
        end
      end presets = [
        {:short_name => "web", :preset_id => "1401103867696-7onx9f"},
        {:short_name => "mobile", :preset_id => "1401103769688-4vb9o5"},
        {:short_name => "medium", :preset_id => "1401104004457-9gjeaw"},
        {:short_name => "small", :preset_id => "1401104111259-i4odaq"},
        {:short_name => "generic_1080p", :preset_id => "1351620000001-000001"},
        {:short_name => "medium_360p", :preset_id => "1416819704726-69zgab"},
        {:short_name => "medium_480p", :preset_id => "1416820003646-62a83m"}
      ]

presets.each do |preset|
        @transcoder.create_job({
          :pipeline_id => pipeline_id,
          :input => {
            :key => full_object_path
          },
          :output => {
            :key => "#{object_path}/processed/file_#{preset[:short_name]}.mp4",
            :thumbnail_pattern => "#{object_path}/thumbnail/#{preset[:short_name]}-{count}",
            :preset_id => preset[:preset_id]
          }
        })
      end number_of_pages = 1
```

```
    upload_all_files(number_of_pages, processing_dir, object_path)

elsif is_audio?(file_extension)

pipeline_id = nil
    @transcoder.list_pipelines.pipelines.each do |p|
      if p.name == bucket_name
        pipeline_id = p.id
      end
    end @transcoder.create_job({
        :pipeline_id => pipeline_id,
        :input => {
          :key => full_object_path
        },
        :output => {
          :key => "#{object_path}/processed/file.mp3",
          :preset_id => "1401104165109-zk9csr"
        }
    })

number_of_pages = 1 make_thumbnails "#{File.expand_path(File.dirname(__FILE__) +
'/../images/')+"/audio.png"}", "#{processing_dir}thumbnail", number_of_pages upload_all_files(number_of_pages, processing_dir, object_path)

elsif is_image?(file_extension)
    command "convert -quality 100 -density 300x300 -resize 1130x989
#{original_file_path} #{processing_dir}processed/page-1.png"

number_of_pages = Dir.glob("#{processing_dir}processed/page-*.png").count make_thumbnails "#{original_file_path}", "#{processing_dir}thumbnail",
number_of_pages
```

```
        upload_all_files(number_of_pages, processing_dir, object_path)

elsif is_office?(file_extension)
        ConvertOffice::ConvertOfficeFormat.new.convert(original_file_path,
"#{processing_dir}tmp/file.pdf")

command "convert -quality 100 -density 300x300 -sharpen 0x1.0 -resize 1130x989
#{processing_dir}tmp/file.pdf #{processing_dir}processed/page-%d.png"
        command "cp #{processing_dir}tmp/file.pdf #{processing_dir}processed/file.pdf"

number_of_pages = Dir.glob("#{processing_dir}processed/page-*.png").count make_thumbnails "#{processing_dir}tmp/file.pdf[0]", "#{processing_dir}thumbnail",
number_of_pages upload_all_files(number_of_pages, processing_dir, object_path)

elsif is_pdf?(file_extension)
        command "convert -quality 100 -density 300x300 -sharpen 0x1.0 -resize 1130x989
#{original_file_path} #{processing_dir}processed/page-%d.png"
        command "cp #{original_file_path} #{processing_dir}processed/file.pdf"

number_of_pages = Dir.glob("#{processing_dir}processed/page-*.png").count make_thumbnails "#{original_file_path}[0]", "#{processing_dir}thumbnail",
number_of_pages upload_all_files(number_of_pages, processing_dir, object_path)

end command "rm -rf #{processing_dir}"
rescue Exception => ex
    print_to_error_log ex.message
```

```ruby
      print_to_error_log ex.backtrace.join("\n")
    end
  end
end def report_status(queue_name, msg, time_started, time_ended, result)
  time_diff_components = Time.diff(time_started, time_ended, '%y, %M, %w, %d and %H:%N:%S')

message = "##############################################################################\n"
  message = message + "File: (#{result ? 'Done' : 'Failed'}@#{msg})\n"
  message = message + "Time taken #{time_diff_components[:diff]}\n"
  message = message + "Started at #{time_started.strftime("%H:%M %p")}\n"
  message = message + "Ended at #{time_ended.strftime("%H:%M %p")}\n"
  message = message + "Status: #{result ? 'Done' : 'Failed'}\n"
  message = message + "##############################################################################\n"

puts message topic = @sns.topics.create(queue_name)
  topic.publish("#{message}\n#{@current_log}", :subject => "Anicaport uploaded file processing #{result ? 'Done' : 'Failed'}.")
  @current_log = ""
end def make_thumbnails(source, destination, number_of_page)
  [{:size=>'200x200', :name=>'mobile-00001'}, {:size=>'200x200', :name=>'web-00001'},
   {:size=>'100x100', :name=>'medium-00001'}, {:size=>'50x50', :name=>'small-00001'}].each do |m|
    command "convert #{source} -gravity center -background white -flatten -alpha off -thumbnail #{m[:size]}^ #{destination}/#{m[:name]}.jpg"
  end
end def upload_all_files(number_of_pages, processing_dir, object_path)
  File.open("#{processing_dir}/pagecount.txt", "w") { |f| f.write("#{number_of_pages}") }
```

```ruby
    toamazon("#{object_path}/pagecount.txt", "#{processing_dir}pagecount.txt")
    for file in Dir.glob("#{processing_dir}processed/*.*")
      toamazon("#{object_path}/processed/#{file.split("/").last}", "#{file}")
    end
    for file in Dir.glob("#{processing_dir}thumbnail/*.*")
      toamazon("#{object_path}/thumbnail/#{file.split("/").last}", "#{file}")
    end
    for file in Dir.glob("#{processing_dir}original/*.*")
      toamazon("#{object_path}/original/#{file.split("/").last}", "#{file}")
    end
end def delete_previous_processing(object_path)
    allobjs = @bucket.objects.with_prefix("#{object_path}/processed").collect(&:key)
    unless allobjs.empty?
      allobjs.each do |key|
        if @bucket.objects["#{key}"].exists?
          print_to_access_log "Deleting file: #{key}"
          @bucket.objects["#{key}"].delete
        end
      end
    end allobjs = @bucket.objects.with_prefix("#{object_path}/thumbnail").collect(&:key)
    unless allobjs.empty?
      allobjs.each do |key|
        if @bucket.objects["#{key}"].exists?
          print_to_access_log "Deleting file: #{key}"
          @bucket.objects["#{key}"].delete
        end
      end
    end
end def toamazon(to, from)
    print_to_access_log "Notice: Uploading #{from} => #{to}."
    @bucket.objects["#{to}"].write(:file => "#{from}", :acl => :private, :server_side_encryption => :aes256)
end def is_image?(file_extension)
    extensions = %w{jpg jpeg gif png tiff bmp dcm}
    extensions.include?(file_extension.downcase)
end
```

```
def is_office?(file_extension)
  extensions = %w{odt sxw rtf doc txt html wiki docx ods sxc xls csv tsv html xlsx swf odp sxi ppt html pptx}
  extensions.include?(file_extension.downcase)
end def is_video?(file_extension)
  extensions = %w{flv m4v mov wmv mp4 mpg mpeg avi}
  extensions.include?(file_extension.downcase)
end def is_audio?(file_extension)
  extensions = %w{mp3 wav wma amr m4a}
  extensions.include?(file_extension.downcase)
end def is_pdf?(file_extension)
  extensions = %w{pdf}
  extensions.include?(file_extension.downcase)
end def scanfile(source)
  str = "clamscan #{source}"
  print_to_access_log "Command: #{str}\n"
  output = Kernel.send(:`, str)
  print_to_access_log "#{output}\n"

if output.include?("Infected files: 0")
    print_to_access_log "Notice: Clean file detected."
    return true
  else
    print_to_error_log "Error: #{result} infection detected."
    return false
  end
end def capture_snapshot(url, file)
  cmd = "#{cutycapt_path} --url='#{url}' --max-wait=10000 --java=off --plugins=off --js-can-open-windows=off --js-can-access-clipboard=off --print-backgrounds=on"
  cmd += " --out='#{file}'"
```

```ruby
    if determine_os == :linux
      xvfb = 'xvfb-run --auto-servernum --server-num=1 --server-args="-screen 0, 1280x800x24" '
      cmd = xvfb.concat(cmd)
    end command cmd
  end def cutycapt_path
    `which cutycapt`.strip or `which CutyCapt`.strip
  end def determine_os
    case RUBY_PLATFORM
      when /darwin/i then :mac
      when /linux/i then :linux
      else raise InvalidOSError, "Currently only works on the Mac and Linux platforms"
    end
  end def command (str)
    print_to_access_log "Command: #{str}\n"
    output = Kernel.send(:`, str)
    print_to_access_log "#{output}\n" if !output.blank?
  end def print_to_access_log(str)
    @current_log = "#{@current_log}#{str}\n"
    puts str
    File.open(File.expand_path(File.dirname(__FILE__) + '/../logs/access.log'), 'a') {|f| f.write("#{str}\n") }
  end def print_to_error_log(str)
    print_to_access_log(str)
    File.open(File.expand_path(File.dirname(__FILE__) + '/../logs/error.log'), 'a') {|f| f.write("#{str}\n") }
  end
end
```

Anicaport
src / Anicaport_destroyer.rb
For delete file
URL: https://github.com/tiatros/Anicaport/blob/master/src/Anicaport_destroyer.rb

```ruby
require File.expand_path(File.dirname(__FILE__) + '/config')
require File.expand_path(File.dirname(__FILE__) + '/../lib/convert_office')

class AnicaportDestroyer def initialize
  queue_name = DELETE_QUEUE

@sqs = AWS::SQS.new
  @s3 = AWS::S3.new
  @sdb = AWS::SimpleDB.new domain = @sdb.domains.create("Anicaport_upload")
  uuids_processing = domain.items['files'].attributes['uuids_processing']
  uuids_failed = domain.items['files'].attributes['uuids_failed']

queue = @sqs.queues.create(queue_name)
  queue.poll(:batch_size => 1) do |msg|
   begin
    if !uuids_processing.values.include?(msg.body)
     uuids_failed.delete msg.body
     self.process_msg(msg.body)
    else
     queue.send_message(msg.body)
     print_to_error_log "Error: File under processing, will try again: #{msg}"
    end
   rescue
   end
  end end def process_msg(msg)
```

```
  bucket_name, object_path = msg.split('::')

unless bucket_name.blank? || object_path.blank?
    print_to_access_log "Notice: Got file to delete: #{msg}"

@bucket = @s3.buckets.create("#{bucket_name}")

allobjs = @bucket.objects.with_prefix(object_path).collect(&:key)
    unless allobjs.empty?
      allobjs.each do |key|
        if @bucket.objects["#{key}"].exists?
          print_to_access_log "Deleting file: #{key}"
          @bucket.objects["#{key}"].delete
        end
      end if @bucket.objects["#{object_path}"].exists?
        print_to_access_log "Deleting file: #{object_path}"
        @bucket.objects["#{object_path}"].delete
      end return true
    else
      print_to_error_log "Error: File does not exist in s3: #{msg}"

return false
    end
  end end def print_to_access_log(str)
  puts str
  File.open(File.expand_path(File.dirname(__FILE__) + '/../logs/access.log'), 'a') {|f| f.write("#{str}\n") }
end def print_to_error_log(str)
  print_to_access_log(str)
  File.open(File.expand_path(File.dirname(__FILE__) + '/../logs/error.log'), 'a') {|f| f.write("#{str}\n") }
```

```
end
end

Anicaport
src / Anicaport_processor.rb
For file processing
URL: https://github.com/tiatros/Anicaport/blob/master/src/Anicaport_processor.rb require File.expand_path(File.dirname(__FILE__) + '/config')
require File.expand_path(File.dirname(__FILE__) + '/../lib/convert_office')

class AnicaportProcessor def initialize
    queue_name = UPLOAD_QUEUE

@sns = AWS::SNS.new
    @sqs = AWS::SQS.new
    @s3 = AWS::S3.new
    @sdb = AWS::SimpleDB.new
    @transcoder = AWS::ElasticTranscoder::Client.new @current_log = ""

domain = @sdb.domains.create(queue_name)
    uuids_processing = domain.items['files'].attributes['uuids_processing']
    uuids_failed = domain.items['files'].attributes['uuids_failed']

queue = @sqs.queues.create(queue_name)
    queue.poll(:batch_size => 1) do |msg| time_started = Time.now
      result = nil begin
        if !uuids_processing.values.include?(msg.body) && !uuids_failed.include?(msg.body)

added_to_db = false
```

```
      begin
        uuids_processing.add msg.body
        added_to_db = true
      rescue Exception => e
        # try next one by clear simpledb
        # uuids_processing.delete
        uuids_failed.delete
      end
      uuids_processing.add msg.body unless added_to_db result = self.process_msg(msg.body)
    end
  rescue Exception => ex
    print_to_error_log ex.message
    print_to_error_log ex.backtrace.join("\n")
    print_to_error_log "Error: Unknown error occurred processing: #{msg}"
  end begin
    uuids_processing.delete msg.body
    uuids_failed.add msg.body if !result self.report_status(queue_name, msg.body, time_started, Time.now, result)
  rescue Exception => ex
  end end
end def process_msg(msg)
  print_to_access_log "Notice: Got message to process: #{msg}"

begin
    url_regexp = /https?:\/\/\w/
    url = msg.split.grep(url_regexp)[0].strip
  rescue
  end unless url.blank?
    print_to_access_log "Notice: Detected URL: #{url}"
    msg = msg.gsub(url, " ").strip
  end
```

```
bucket_name, full_object_path = msg.split('::')

print_to_access_log "bucket: #{bucket_name}"
print_to_access_log "full_object_path: #{full_object_path}"
print_to_access_log "url: #{url}" unless url.blank?

unless bucket_name.blank? || full_object_path.blank?
  @bucket = @s3.buckets.create("#{bucket_name}")
  if @bucket.objects["#{full_object_path}"].exists?
    process_file(bucket_name, full_object_path)
    return true
  elsif !url.blank?
    process_url(bucket_name, full_object_path, url)
    return true
  else
    print_to_error_log "Error: File does not exist in s3: #{msg}"
    return false
  end
end
end def process_url(bucket_name, full_object_path, url)
  print_to_access_log "Notice: Processing URL: #{url}"

redirected_url = url begin
    redirected_url = open(redirected_url).base_uri.to_s
  rescue
    redirected_url = nil
  end url = redirected_url object_path_arr = full_object_path.split("/")
  if object_path_arr[0]=="common"
    object_uuid = object_path_arr[1]
    file_name = object_path_arr[3]
    provider_folder = object_path_arr[0]
```

```
else
  object_uuid = object_path_arr[2]
  file_name = object_path_arr[4]
  provider_folder = object_path_arr[1]
end file_basename = file_name.split('.').first
file_extension = file_name.split('.').last account_dir = File.expand_path(File.dirname(__FILE__) + '/../kitchen/' +
provider_folder)+"/"
  processing_dir = "#{account_dir}#{object_uuid}/"
  original_file_path = "#{processing_dir}original/#{file_name}"

command "mkdir #{account_dir}" if File.exists?(account_dir) == false
command "mkdir #{processing_dir}" if File.exists?(processing_dir) == false
command "mkdir #{processing_dir}original/" if File.exists?("#{processing_dir}original/") ==
false
command "mkdir #{processing_dir}processed/" if
File.exists?("#{processing_dir}processed/") == false
command "mkdir #{processing_dir}thumbnail/" if
File.exists?("#{processing_dir}thumbnail/") == false
command "mkdir #{processing_dir}tmp/" if File.exists?("#{processing_dir}tmp/") == false unless redirected_url.blank?
  capture_snapshot(url, original_file_path)
else
  command "cp #{File.expand_path(File.dirname(__FILE__) + '/../images/')+"/404.jpg"}
#{original_file_path}"
end snapshop_created = false
if File.exists?(original_file_path)
  command "convert #{original_file_path} -thumbnail '500x500^' -background white -flatten
-alpha off -gravity center -extent 500x500
#{processing_dir}tmp/#{file_basename}.#{file_extension}"
  command "cp #{processing_dir}tmp/#{file_basename}.#{file_extension}
#{original_file_path}"

toamazon("#{full_object_path}", "#{original_file_path}")
snapshop_created = true
end
```

```
command "rm -rf #{processing_dir}"

process_file(bucket_name, full_object_path) if snapshop_created
end def process_file(bucket_name, full_object_path)
  print_to_access_log "Notice: Processing FILE: #{full_object_path}"

object_path_arr = full_object_path.split("/")
  if object_path_arr[0]=="common"
    object_uuid = object_path_arr[1]
    file_name = object_path_arr[3]
    provider_folder = "#{object_path_arr[0]}"
  else
    object_uuid = object_path_arr[2]
    file_name = object_path_arr[4]
    provider_folder = "#{object_path_arr[0]}/#{object_path_arr[1]}"
  end object_path = "#{provider_folder}/#{object_uuid}"

file_basename = file_name.split('.').first
  file_extension = file_name.split('.').last account_dir = File.expand_path(File.dirname(__FILE__) + '/../kitchen/' + provider_folder)+"/"
  processing_dir = "#{account_dir}#{object_uuid}/"
  original_file_path = "#{processing_dir}original/#{file_name}"

command "mkdir #{account_dir}" if File.exists?(account_dir) == false
  command "mkdir #{processing_dir}" if File.exists?(processing_dir) == false
  command "mkdir #{processing_dir}original/" if File.exists?("#{processing_dir}original/") == false
  command "mkdir #{processing_dir}processed/" if File.exists?("#{processing_dir}processed/") == false
  command "mkdir #{processing_dir}thumbnail/" if File.exists?("#{processing_dir}thumbnail/") == false
  command "mkdir #{processing_dir}tmp/" if File.exists?("#{processing_dir}tmp/") == false
```

```ruby
chunk_size = 5_242_880 obj = @bucket.objects["#{full_object_path}"]
size = obj.content_length
byte_offset = 0

File.open(original_file_path, 'w') do |file|
  while byte_offset < size
    range = "bytes=#{byte_offset}-#{byte_offset + chunk_size - 1}"
    file.write(obj.read(:range => range))
    byte_offset += chunk_size
  end
end if scanfile(original_file_path)
  begin delete_previous_processing(object_path)

if is_video?(file_extension)

pipeline_id = nil
      @transcoder.list_pipelines.pipelines.each do |p|
        if p.name == bucket_name
          pipeline_id = p.id
        end
      end presets = [
        {:short_name => "web", :preset_id => "1401103867696-7onx9f"},
        {:short_name => "mobile", :preset_id => "1401103769688-4vb9o5"},
        {:short_name => "medium", :preset_id => "1401104004457-9gjeaw"},
        {:short_name => "small", :preset_id => "1401104111259-i4odaq"},
        {:short_name => "generic_1080p", :preset_id => "1351620000001-000001"},
        {:short_name => "medium_360p", :preset_id => "1416819704726-69zgab"},
        {:short_name => "medium_480p", :preset_id => "1416820003646-62a83m"}
      ]
```

```
presets.each do |preset|
  @transcoder.create_job({
    :pipeline_id => pipeline_id,
    :input => {
      :key => full_object_path
    },
    :output => {
      :key => "#{object_path}/processed/file_#{preset[:short_name]}.mp4",
      :thumbnail_pattern => "#{object_path}/thumbnail/#{preset[:short_name]}-{count}",
      :preset_id => preset[:preset_id]
    }
  })
end number_of_pages = 1 upload_all_files(number_of_pages, processing_dir, object_path)

elsif is_audio?(file_extension)

pipeline_id = nil
@transcoder.list_pipelines.pipelines.each do |p|
  if p.name == bucket_name
    pipeline_id = p.id
  end
end @transcoder.create_job({
  :pipeline_id => pipeline_id,
  :input => {
    :key => full_object_path
  },
  :output => {
    :key => "#{object_path}/processed/file.mp3",
    :preset_id => "1401104165109-zk9csr"
  }
})

number_of_pages = 1
```

```
        make_thumbnails "#{File.expand_path(File.dirname(__FILE__) +
'/../images/')+"/audio.png"}", "#{processing_dir}thumbnail", number_of_pages upload_all_files(number_of_pages, processing_dir, object_path)

elsif is_image?(file_extension)
        command "convert -quality 100 -density 300x300 -resize 1130x989
#{original_file_path} #{processing_dir}processed/page-1.png"

number_of_pages = Dir.glob("#{processing_dir}processed/page-*.png").count make_thumbnails "#{original_file_path}", "#{processing_dir}thumbnail",
number_of_pages upload_all_files(number_of_pages, processing_dir, object_path)

elsif is_office?(file_extension)
        ConvertOffice::ConvertOfficeFormat.new.convert(original_file_path,
"#{processing_dir}tmp/file.pdf")

command "convert -quality 100 -density 300x300 -sharpen 0x1.0 -resize 1130x989
#{processing_dir}tmp/file.pdf #{processing_dir}processed/page-%d.png"
        command "cp #{processing_dir}tmp/file.pdf #{processing_dir}processed/file.pdf"

number_of_pages = Dir.glob("#{processing_dir}processed/page-*.png").count make_thumbnails "#{processing_dir}tmp/file.pdf[0]", "#{processing_dir}thumbnail",
number_of_pages upload_all_files(number_of_pages, processing_dir, object_path)

elsif is_pdf?(file_extension)
        command "convert -quality 100 -density 300x300 -sharpen 0x1.0 -resize 1130x989
#{original_file_path} #{processing_dir}processed/page-%d.png"
        command "cp #{original_file_path} #{processing_dir}processed/file.pdf"
```

```
    number_of_pages = Dir.glob("#{processing_dir}processed/page-*.png").count make_thumbnails "#{original_file_path}[0]", "#{processing_dir}thumbnail", number_of_pages upload_all_files(number_of_pages, processing_dir, object_path)

end command "rm -rf #{processing_dir}"
   rescue Exception => ex
    print_to_error_log ex.message
    print_to_error_log ex.backtrace.join("\n")
   end
  end
end def report_status(queue_name, msg, time_started, time_ended, result)
   time_diff_components = Time.diff(time_started, time_ended, '%y, %M, %w, %d and %H:%N:%S')

message = "############################################################################\n"
   message = message + "File: (#{result ? 'Done' : 'Failed'}@#{msg})\n"
   message = message + "Time taken #{time_diff_components[:diff]}\n"
   message = message + "Started at #{time_started.strftime("%H:%M %p")}\n"
   message = message + "Ended at #{time_ended.strftime("%H:%M %p")}\n"
   message = message + "Status: #{result ? 'Done' : 'Failed'}\n"
   message = message + "############################################################################\n"

puts message topic = @sns.topics.create(queue_name)
   topic.publish("#{message}\n#{@current_log}", :subject => "Anicaport uploaded file processing #{result ? 'Done' : 'Failed'}.")
```

```
@current_log = ""
end def make_thumbnails(source, destination, number_of_page)
  [{:size=>'200x200', :name=>'mobile-00001'}, {:size=>'200x200', :name=>'web-00001'},
{:size=>'100x100', :name=>'medium-00001'}, {:size=>'50x50', :name=>'small-00001'}].each
do |m|
    command "convert #{source} -gravity center -background white -flatten -alpha off -
thumbnail #{m[:size]}^ #{destination}/#{m[:name]}.jpg"
  end
end def upload_all_files(number_of_pages, processing_dir, object_path)
  File.open("#{processing_dir}/pagecount.txt", "w") { |f| f.write("#{number_of_pages}") } toamazon("#{object_path}/pagecount.txt", "#{processing_dir}pagecount.txt")
  for file in Dir.glob("#{processing_dir}processed/*.*")
    toamazon("#{object_path}/processed/#{file.split("/").last}", "#{file}")
  end
  for file in Dir.glob("#{processing_dir}thumbnail/*.*")
    toamazon("#{object_path}/thumbnail/#{file.split("/").last}", "#{file}")
  end
  for file in Dir.glob("#{processing_dir}original/*.*")
    toamazon("#{object_path}/original/#{file.split("/").last}", "#{file}")
  end
end def delete_previous_processing(object_path)
  allobjs = @bucket.objects.with_prefix("#{object_path}/processed").collect(&:key)
  unless allobjs.empty?
    allobjs.each do |key|
      if @bucket.objects["#{key}"].exists?
        print_to_access_log "Deleting file: #{key}"
        @bucket.objects["#{key}"].delete
      end
    end
  end allobjs = @bucket.objects.with_prefix("#{object_path}/thumbnail").collect(&:key)
  unless allobjs.empty?
    allobjs.each do |key|
      if @bucket.objects["#{key}"].exists?
        print_to_access_log "Deleting file: #{key}"
```

```ruby
        @bucket.objects["#{key}"].delete
      end
    end
  end
end def toamazon(to, from)
  print_to_access_log "Notice: Uploading #{from} => #{to}."
  @bucket.objects["#{to}"].write(:file => "#{from}", :acl => :private, :server_side_encryption => :aes256)
end def is_image?(file_extension)
  extensions = %w{jpg jpeg gif png tiff bmp dcm}
  extensions.include?(file_extension.downcase)
end def is_office?(file_extension)
  extensions = %w{odt sxw rtf doc txt html wiki docx ods sxc xls csv tsv html xlsx swf odp sxi ppt html pptx}
  extensions.include?(file_extension.downcase)
end def is_video?(file_extension)
  extensions = %w{flv m4v mov wmv mp4 mpg mpeg avi}
  extensions.include?(file_extension.downcase)
end def is_audio?(file_extension)
  extensions = %w{mp3 wav wma amr m4a}
  extensions.include?(file_extension.downcase)
end def is_pdf?(file_extension)
  extensions = %w{pdf}
  extensions.include?(file_extension.downcase)
end def scanfile(source)
  str = "clamscan #{source}"
  print_to_access_log "Command: #{str}\n"
```

```
output = Kernel.send(:`, str)
print_to_access_log "#{output}\n"

if output.include?("Infected files: 0")
  print_to_access_log "Notice: Clean file detected."
  return true
else
  print_to_error_log "Error: #{result} infection detected."
  return false
end
end def capture_snapshot(url, file)
  cmd = "#{cutycapt_path} --url='#{url}' --max-wait=10000 --java=off --plugins=off --js-can-open-windows=off --js-can-access-clipboard=off --print-backgrounds=on"
  cmd += " --out='#{file}'"

if determine_os == :linux
    xvfb = 'xvfb-run --auto-servernum --server-num=1 --server-args="-screen 0, 1280x800x24" '
    cmd = xvfb.concat(cmd)
  end command cmd
end def cutycapt_path
  `which cutycapt`.strip or `which CutyCapt`.strip
end def determine_os
  case RUBY_PLATFORM
    when /darwin/i then :mac
    when /linux/i then :linux
    else raise InvalidOSError, "Currently only works on the Mac and Linux platforms"
  end
end def command (str)
  print_to_access_log "Command: #{str}\n"
  output = Kernel.send(:`, str)
```

```ruby
    print_to_access_log "#{output}\n" if !output.blank?
  end def print_to_access_log(str)
    @current_log = "#{@current_log}#{str}\n"
    puts str
    File.open(File.expand_path(File.dirname(__FILE__) + '/../logs/access.log'), 'a') {|f|
f.write("#{str}\n") }
  end def print_to_error_log(str)
    print_to_access_log(str)
    File.open(File.expand_path(File.dirname(__FILE__) + '/../logs/error.log'), 'a') {|f|
f.write("#{str}\n") }
  end
end
```

Anicaport
src / Anicaport_destroyer.rb
For delete file
URL: https://github.com/tiatros/Anicaport/blob/master/src/Anicaport_destroyer.rb

```ruby
require File.expand_path(File.dirname(__FILE__) + '/config')
require File.expand_path(File.dirname(__FILE__) + '/../lib/convert_office')

class AnicaportDestroyer def initialize
    queue_name = DELETE_QUEUE

@sqs = AWS::SQS.new
    @s3 = AWS::S3.new
    @sdb = AWS::SimpleDB.new domain = @sdb.domains.create("Anicaport_upload")
    uuids_processing = domain.items['files'].attributes['uuids_processing']
    uuids_failed = domain.items['files'].attributes['uuids_failed']

queue = @sqs.queues.create(queue_name)
```

```ruby
    queue.poll(:batch_size => 1) do |msg|
      begin
        if !uuids_processing.values.include?(msg.body)
          uuids_failed.delete msg.body
          self.process_msg(msg.body)
        else
          queue.send_message(msg.body)
          print_to_error_log "Error: File under processing, will try again: #{msg}"
        end
      rescue
      end
    end end def process_msg(msg)
  bucket_name, object_path = msg.split('::')

unless bucket_name.blank? || object_path.blank?
    print_to_access_log "Notice: Got file to delete: #{msg}"

@bucket = @s3.buckets.create("#{bucket_name}")

allobjs = @bucket.objects.with_prefix(object_path).collect(&:key)
    unless allobjs.empty?
      allobjs.each do |key|
        if @bucket.objects["#{key}"].exists?
          print_to_access_log "Deleting file: #{key}"
          @bucket.objects["#{key}"].delete
        end
      end if @bucket.objects["#{object_path}"].exists?
      print_to_access_log "Deleting file: #{object_path}"
      @bucket.objects["#{object_path}"].delete
    end return true
  else
    print_to_error_log "Error: File does not exist in s3: #{msg}"

return false
```

```
    end
  end end def print_to_access_log(str)
  puts str
  File.open(File.expand_path(File.dirname(__FILE__) + '/../logs/access.log'), 'a') {|f| f.write("#{str}\n") }
end def print_to_error_log(str)
  print_to_access_log(str)
  File.open(File.expand_path(File.dirname(__FILE__) + '/../logs/error.log'), 'a') {|f| f.write("#{str}\n") }
end
end
```

The invention claimed is:

1. In a computer network comprising a processor in communication with one or more tangible computer-readable non-transitory storage media comprising computer-executable instructions operable to, when executed by the processor, enable the at least one computer processor to implement a method, the method comprising:
   receiving an ingest request from a first user having a medical image to share with a second user within a Carepod created for a patient receiving medical treatment;
   transcoding the medical image into one of a plurality of image formats;
   associate any metadata from transcoding with the transcoded medical image;
   if the first user is not a member of the Carepod, adding the first user to the Carepod by request of the second user;
   authenticating the first user by request of the second user as a member of the Carepod, authenticating the first user further comprising:
      receiving a request for user creation from the second user for the first user;
      generating a security token and associating the security token with a communication back to the first user as follows:
   generating a first security token;
   associating the first security token with an email address of the first user;
   sending an email to the first user to confirm the email address;
   receiving confirmation from first user with a confirmation token and a second means of communication to first user specified;
      verifying the confirmation token from the first user against the security token;
   generating a second security token back to first user via the second means of communication;
   and verifying the second security token received by the first user;
   granting a set of privileges to the first user for interacting with medical images within the Carepod;
   depending upon the set of privileges granted the first user, receiving medical image data from the first user; and
   sharing the medical image with the second user within the Carepod.

2. The method of claim 1 wherein adding the first user to the Carepod further comprises:
   receiving data regarding a second communications pathway for the first user;
   sending a second part authentication token to the second communication pathway;
   receiving the second part authentication token from the first user; and
   verifying the second part authentication token.

3. The method of claim 1 wherein sharing the medical image with the second user within the Carepod further comprises: uploading a medical image to the Carepod.

4. The method of claim 3 wherein uploading a medical image to the Carepod further comprises: storing the medical image for asynchronous sharing of the medical image with the second user.

5. The method of claim 3 wherein uploading a medical image to the Carepod further comprises: streaming the medical image to the second user.

6. The method of claim 5 wherein streaming the medical image to the second user further comprises: sharing the medical image in substantially real-time with the second user.

7. A system for sharing medical image data of a patient receiving medical treatment, wherein said patients and their caregivers are members of a trusted community of a Carepod, the system comprising:
   a processor;
   non-transitory computer-readable storage encoded with instructions that, when executed on the processor, implement the following modules:
   a Carepod module, said Carepod module configured to receiving communications from a remote device of a first user, the first user having a medical image to share with a second user of a Carepod, the Carepod created for a patient receiving medical treatment;
   a transcoding module, said transcoding module configured to transcode the medical image into one of a plurality of image formats and associate any metadata from transcoding with the transcoded medical image;
   a user authentication module, said user authentication module configured to authenticating the first user as a member of the Carepod by performing the following:
      receiving a request for user creation from the second user for the first user;
      generating a first security token and associating the security token with a communication back to the first user;
   associating the first security token with an email address of the first user;
   sending an email to the first user to confirm the email address;
   receiving confirmation from first user with a confirmation token and a second means of communication to first user specified;
      verifying the confirmation token from the first user against the first security token;
   generating a second security token back to first user via the second means of communication;
   and verifying the second security token received by the first user;
   a user privileges module, said user privileges module configured to set privileges of the first user to perform actions regarding medical images of the patient.

8. The system as recited in claim 7 wherein said system is configured to verify a confirmation from the first user against the first security token.

9. The system as recited in claim 8 wherein said system is configured to receive data regarding a second communications pathway for the first user; send a second part authentication token to the second communication pathway; and receive the second part authentication token from the first user; and verifying the second part authentication token.

10. The system as recited in claim 7 wherein said system is configured to store the medical image for asynchronous sharing of the medical image with the second user.

11. The system as recited in claim 7 wherein said system is configured to stream the medical image to the second user in substantially real-time.

* * * * *